(12) United States Patent
Rosenblatt et al.

(10) Patent No.: US 11,826,332 B2
(45) Date of Patent: Nov. 28, 2023

(54) ANTIMICROBIAL COMPOSITIONS AND USES THEREOF

(71) Applicant: Board of Regents, The University of Texas System, Austin, TX (US)

(72) Inventors: Joel Rosenblatt, Pottstown, PA (US); Issam Raad, Missouri City, TX (US)

(73) Assignee: Board of Regents, The University of Texas System, Austin, TX (US)

(*) Notice: Subject to any disclaimer, the term of this patent is extended or adjusted under 35 U.S.C. 154(b) by 177 days.

(21) Appl. No.: 17/360,966

(22) Filed: Jun. 28, 2021

(65) Prior Publication Data

US 2022/0087963 A1    Mar. 24, 2022

Related U.S. Application Data

(62) Division of application No. 16/078,735, filed as application No. PCT/US2017/018704 on Feb. 21, 2017, now Pat. No. 11,065,223.

(60) Provisional application No. 62/298,082, filed on Feb. 22, 2016.

(51) Int. Cl.

| | | |
|---|---|---|
| *A61K 31/20* | (2006.01) | |
| *A61K 45/06* | (2006.01) | |
| *A61K 31/21* | (2006.01) | |
| *A61K 31/715* | (2006.01) | |
| *A61K 31/732* | (2006.01) | |
| *C08L 5/00* | (2006.01) | |
| *C08L 5/06* | (2006.01) | |
| *C08L 5/08* | (2006.01) | |
| *C08L 89/00* | (2006.01) | |
| *A61L 29/04* | (2006.01) | |
| *A61L 29/16* | (2006.01) | |
| *A61K 33/40* | (2006.01) | |
| *A61P 31/02* | (2006.01) | |
| *A61D 7/00* | (2006.01) | |
| *A61M 3/02* | (2006.01) | |
| *A61M 25/00* | (2006.01) | |
| *A61M 25/10* | (2013.01) | |
| *A61M 39/22* | (2006.01) | |

(52) U.S. Cl.
CPC .............. *A61K 31/20* (2013.01); *A61D 7/00* (2013.01); *A61K 31/21* (2013.01); *A61K 31/715* (2013.01); *A61K 31/732* (2013.01); *A61K 33/40* (2013.01); *A61K 45/06* (2013.01); *A61L 29/043* (2013.01); *A61L 29/16* (2013.01); *A61M 3/0262* (2013.01); *A61M 3/0283* (2013.01); *A61M 25/0017* (2013.01); *A61M 25/1011* (2013.01); *A61M 39/22* (2013.01); *A61P 31/02* (2018.01); *C08L 5/00* (2013.01); *C08L 5/06* (2013.01); *C08L 5/08* (2013.01); *C08L 89/00* (2013.01); *A61L 2300/404* (2013.01); *A61L 2300/406* (2013.01); *A61M 2210/0693* (2013.01); *A61M 2210/1082* (2013.01); *A61M 2210/1089* (2013.01); *A61M 2210/12* (2013.01); *A61M 2250/00* (2013.01)

(58) Field of Classification Search
CPC ........ A61K 31/20; A61K 45/06; A61K 31/21; A61K 31/715; A61K 31/732; A61K 29/16; C08L 5/00; C08L 5/06; C08L 5/08; C08L 89/00; A61L 29/00; A61L 29/043; A61L 2300/404; A61L 2300/406; A61P 31/02; A61D 7/00; A61M 3/0262; A61M 3/0283; A61M 25/0017; A61M 25/1011; A61M 39/22; A61M 2210/406; A61M 2210/0693; A61M 2210/1089; A61M 2210/12; A61M 2250/00
See application file for complete search history.

(56) References Cited

U.S. PATENT DOCUMENTS

| | | |
|---|---|---|
| 3,593,713 A | 7/1971 | Bogoff et al. |
| 4,211,233 A | 7/1980 | Lin |
| 4,479,795 A | 10/1984 | Mustacich et al. |
| 4,489,097 A | 12/1984 | Stone |
| 5,217,493 A | 6/1993 | Raad et al. |
| 5,364,356 A | 11/1994 | Hoefling |
| 5,460,802 A | 10/1995 | Asami et al. |
| 5,624,704 A | 4/1997 | Darouiche et al. |
| 5,648,389 A | 7/1997 | Gans et al. |
| 5,681,802 A | 10/1997 | Fujiwara et al. |
| 5,902,283 A | 5/1999 | Darouiche et al. |
| 6,210,392 B1 | 4/2001 | Vigil et al. |
| 7,651,661 B2 | 1/2010 | Raad et al. |

(Continued)

FOREIGN PATENT DOCUMENTS

| | | |
|---|---|---|
| CN | 104798789 | 7/2015 |
| DE | 20 2013 001998 | 4/2014 |

(Continued)

OTHER PUBLICATIONS

"Prodn. of mono- and oligo-galacturonic acid for resisting infections—from pectin or pectic acid, using enzyme fixed to carrier," XP002233978, Derwent, 1994.

Becker et al., "Final Report of the Safety Assessment of Allantoin and Its Related Complexes", *Int J Toxicol.* 29(3 Suppl):84S-97S, 2010.

De Gomes et al., "Cytotoxicity of denture adhesives", *Clin Oral Investig*, 15:885-893, 2011.

(Continued)

*Primary Examiner* — Shirley V Gembeh

(74) *Attorney, Agent, or Firm* — Parker Highlander PLLC

(57) ABSTRACT

In some aspects, provided herein are antimicrobial compositions comprising partially esterified polygalacturonic acid and certain fatty acids (e.g., caprylic acid). In some embodiments, the antimicrobial composition may be administered (e.g., topically or orally) to a subject, such as a human patient to treat an infection (e.g., an infection comprising a biofilm). In some aspects, improved catheters are provided.

23 Claims, 4 Drawing Sheets

(56) References Cited

U.S. PATENT DOCUMENTS

| | | |
|---|---|---|
| 8,137,705 B2 | 3/2012 | Doyle et al. |
| 9,457,002 B2 | 10/2016 | Raad et al. |
| 2001/0041859 A1 | 11/2001 | Vigil et al. |
| 2003/0078242 A1 | 4/2003 | Raad et al. |
| 2005/0197634 A1 | 9/2005 | Raad et al. |
| 2007/0154621 A1 | 7/2007 | Raad |
| 2008/0183152 A1 | 7/2008 | Raad et al. |
| 2010/0055086 A1 | 3/2010 | Raad |
| 2011/0201692 A1 | 8/2011 | Raad |
| 2011/0213025 A1 | 9/2011 | Finch |
| 2011/0311602 A1 | 12/2011 | Mills et al. |
| 2012/0064372 A1 | 3/2012 | Raad |
| 2012/0282207 A1 | 11/2012 | Lutz |
| 2012/0282356 A1 | 11/2012 | Schrader |
| 2012/0289591 A1 | 11/2012 | Folan |
| 2015/0196523 A1 | 7/2015 | Raad et al. |

FOREIGN PATENT DOCUMENTS

| | | | |
|---|---|---|---|
| GB | 1283892 | | 8/1972 |
| JP | H10-226701 | | 8/1998 |
| JP | 2002-238909 | | 8/2002 |
| JP | 2014-076162 | | 5/2014 |
| WO | WO 1999/007420 | | 2/1999 |
| WO | WO 2014/025994 | | 2/2014 |
| WO | WO 2014025994 | * | 2/2014 |

OTHER PUBLICATIONS

Demidenko, "Sample size and optimal design for logistic regression with binary interaction", Stat. Med., 27:36-46, 2008.
Evans et al., "Measurement of gastrointestinal pH profiles in normal ambulant human subjects", Gut. 29(8):1035-41, 1988.
Extended European Search Report issued in European Application No. 177570652, dated Feb. 17, 2020.
Fenton et al., "0.4% Nitroglycerin Ointment", Drugs 66:343-349, 2006.
Haidukewych et al., "Monitoring octanoic and decanoic acids in plasma from children with intractable epilepsy treated with medium-chain triglyceride diet", Clin Chem. 28(4):642-645, 1982.
Han et al., "Nitric oxide-releasing nanoparticles accelerate wound healing by promoting fibroblast migration and collagen deposition", Am J Pathol 180:1465-1473, 2012.
James et al., "Biofilms in chronic wounds", Wound Repair Regen 16:37-44, 2008.
Karanlik et al., "The effect of glyceryl trinitrate ointment on posthemorrhoidectomy pain and wound healing: results of a randomized, double-blind, placebo-controlled study", Dis Colon Rectum 52:280-285, 2009.
Kuhn et al., "Antifungal susceptibility of Candida biofilms: unique efficacy of amphotericin B lipid formulations and echinocandins", Antimicrob Agents Chemother., 46(6):1773-1780, 2002.
Lambers et al., "Natural skin surface pH is on average below 5, which is beneficial for its resident flora", Int J Cosmet Sci. 28(5):359-70, 2006.
Lang, "Vaginal acidity and pH. A review", Obstet Gynecol Surv. 10(4):546-60, 1955.
Munarin et al., "Advances in biomedical applications of pectin gels", Int J Biol Macromol. 51(4):681-9, 2012.
O'Brien et al., "Investigation of the Alamar Blue (resazurin) fluorescent dye for the assessment of mammalian cell cytotoxicity", Eur J Biochem, 267:5421-5426, 2000.
Office Action issued in European Application No. 177570652, dated Jan. 26, 2021.
Office Action issued in Japanese Application No. 2018-563388, dated Jan. 25, 2021, and English translation thereof.
Office Action issued in Japanese Application No. 2021-150725, dated Feb. 6, 2023, and English translation thereof.
Office Action issued in Japanese Application No. 2021-150725, dated Oct. 3, 2022, and English translation thereof.
Office Action issued in U.S. Appl. No. 16/078,735 dated Apr. 15, 2020.
Office Action issued in U.S. Appl. No. 16/078,735 dated Sep. 14, 2020.
PCT International Preliminary Report on Patentability issued in corresponding PCT Application No. PCT/US2017/018704, dated Aug. 28, 2018.
PCT International Search Report and Written Opinion issued in corresponding PCT Application No. PCT/US2017/018704, dated Jun. 16, 2017.
Pieper and Caliri, "Nontraditional wound care: A review of the evidence for the use of sugar, papaya/papain, and fatty acids", J Wound Ostomy Continence Nurs 30(4):175-183, 2003.
Rayyan et al., "Short-Term Use of Parenteral Nutrition With a Lipid Emulsion Containing a Mixture of Soybean Oil, Olive Oil, Medium—Chain Triglycerides, and Fish Oil", J Parenter Enteral Nutr. 36(1 Suppl):81S-94S, 2012.
Robson, "Wound infection: a failure of wound healing caused by an imbalance of bacteria", Surg Clin North Am 77:637-650, 1997.
Rosenblatt et al., "Caprylic acid and glyceryl trinitrate combination for eradication of biofilm", Antimicrob Agents Chemother, 59:1786-1788, 2015.
Rosenblatt et al., "Efficacy of a novel synergistic polygalacturonic + caprylic acid + nitroglycerin antimicrobial wound ointment against common wound pathogens in a time-to-kill biofilm eradication model," Session 247, Poster Abstract, 3(Suppl 1):2256, 2016.
Rosenblatt et al., "Glyceryl trinitrate complements citrate and ethanol in a novel antimicrobial catheter lock solution to eradicate biofilm organisms", Antimicrob Agents Chemother. 57(8):3555-3560, 2013.
Schierle et al., "Staphylococcal biofilms impair wound healing by delaying reepithelialization in a murine cutaneous wound model", Wound Repair Regen 17:354-359, 2009.
Siddiqui and Bernstein, "Chronic wound infection: facts and controversies", Clin Dermotol 28:519-526, 2010.
Skriyanoya and Marounek, "Influence of pH on antimicrobial activity of organic acids against rabbit enteropathogenic strain of Escherichia coli", Folia Microbiol (Praha). 52(1):70-2, 2007.
Sriamornsak, "Chemistry of pectin and its pharmaceutical uses: A review ", Silpokorn Univ. J., 3(1-2):206-228, 2003.
Srivastava er al., "Burn wound healing property of Cocos nucifera: An appraisal", Indian J Pharmacol. 40(4):144-6, 2008.
Strober, "Trypan Blue Exclusion Test of Cell Viability", Curr Protoc Immunol, 111:A3.B.1-A3.B.3, 2015.
Supplementary European Search Report issued in European Application No. 17757065.2, dated Oct. 11, 2019.
Thakur er al., "Chemistry and uses of pectin—a review", Crit Rev Food Sci Nutr. 37(1):47-73, 1997.
Wanten and Calder, "Immune modulation by parenteral lipid emulsions", Am J Clin Nutr. 85(5):1171-1184, 2007.
Yang er al., "Anti-Escherichia coli O157:H7 actiVity of free fatty acids under varying pH", Can J Microbiol. 56(3):263-7, 2010.

* cited by examiner

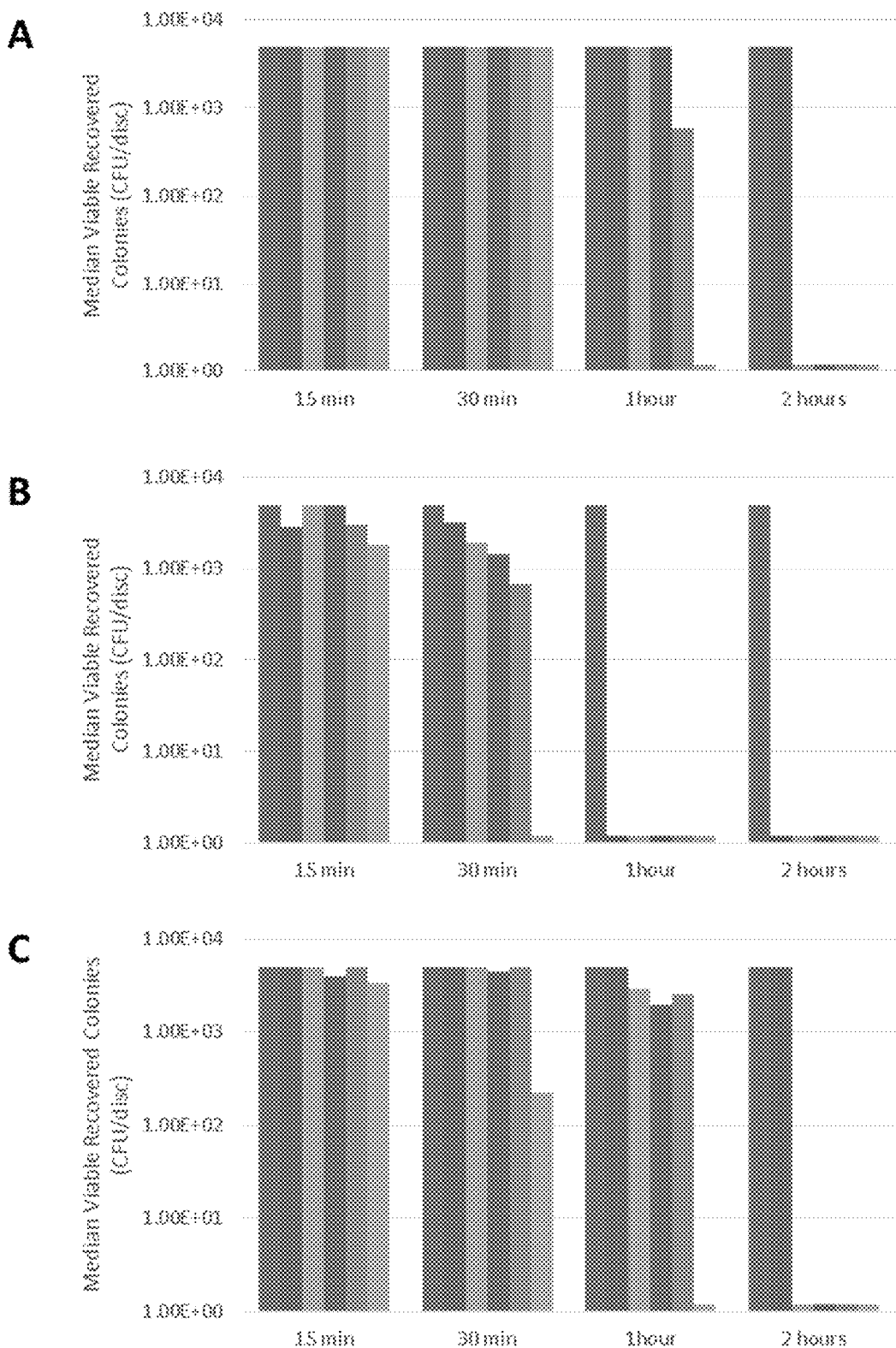
FIGS. 1A-C

ANTIMICROBIAL COMPOSITIONS AND USES THEREOF

This application is a divisional of U.S. application Ser. No. 16/078,735, filed Aug. 22, 2018, which is a national phase application under 35 U.S.C. § 371 of International Application No. PCT/US2017/018704, filed Feb. 21, 2017, which claims the benefit of U.S. Provisional Application Ser. No. 62/298,082, filed on Feb. 22, 2016, the entirety of each of which is incorporated herein by reference.

BACKGROUND OF THE INVENTION

1. Field of the Invention

The present invention relates generally to the field of molecular biology and medicine. More particularly, it concerns antimicrobial compositions.

2. Description of Related Art

The care and management of patients with chronic wounds especially those with cancer remain a major challenge for both the patient and the clinicians. Further complicating this situation is the paucity of evidence-based treatment strategies for chronic wound care. An increase in the number of patients with chronic wound has been reported as a result of an increase in the cancer patient population as well as those with advancing age. It has been estimated that approximately 1% of the population will develop leg ulceration in the course of their lifetime. In the United States alone, chronic wounds affect 3 to 6 million patients annually with an estimated treatment cost of $5 to $10 billion each year. Wounds can be difficult to heal due to the presence of biofilms particularly in immunocompromised cancer patients. This coupled with the increasing emergence of antibiotic resistance-biofilm adversely impacts the outcomes of antibiotic wound therapies.

A review of the current practice advocate that systemically administered antibiotics alone did not effectively decrease bacterial levels in granulating wounds whereas topically applied antimicrobial can be effective in improving patient outcome. Topical disinfection of skin and wounds, particularly microbially contaminated wounds, remains an important healthcare need for preventing infections. Additionally, disinfection of medical devices, including indwelling ones, and implantation sites (such as surgical sites) to prevent infections remains a significant healthcare need. Clearly, there is a need for new and improved antimicrobial compositions and methods of disinfecting surfaces and treating infections.

SUMMARY OF THE INVENTION

In some aspects, the present invention overcomes limitations in the prior art by providing new and improved antimicrobial compositions. The present invention is based, in part, of the discovery that polygalacturonic acid mixture such as partially esterified polygalacturonic acid and a fatty acid (e.g., caprylic acid) can synergistically function to enhance microbial compositions. Methods of using the antimicrobial compositions including, e.g., treating wounds and disinfecting surgical devices, skin, wounds, surgical sites, and surfaces are also provided. In some embodiments, antimicrobial compositions provided herein can be applied topically or to the skin or other tissue of a subject, such as a mammal or human to provide a therapeutic effect (e.g., cleaning a wound or surgical site, disinfection of microbes, promoting healing, and/or reducing pain).

In some aspects, provided herein are synergistic antimicrobial compositions comprising partially esterified polygalacturonic acid (partially esterified PGA) and a fatty acid (e.g., a protonated saturated fatty acids such as caprylic acid) that can treat or eradicate biofilms. In some embodiments, the concentrations of the partially esterified PGA and the fatty acid are sufficiently low such that little or no associated toxicities are observed when the antimicrobial composition is administered to a human. In some embodiments, an enhancers such as a peroxide (e.g., hydrogen peroxide) and a nitric oxide donors (e.g., a glyceryl nitrate such as, for example glyceryl trinitrate) can be added to accelerate antimicrobial action. A chelator (e.g., EDTA, citrate, etc.) may be included in an antimicrobial composition as described herein, e.g., to improve antimicrobial activity and/or maintain desired local pHs. In addition, one or more thickener, gelling agent, emollient, surfactant, humectant, moisturizer, anti-inflammatory agent, coloring or tinting agents, and/or fragrances can be added to an antimicrobial composition as described herein, e.g., to improve handling properties for specific applications. In some embodiments, an antiseptic composition of the present invention may be used for (1) topical disinfection of skin and wounds, such as microbially contaminated wounds, as well as (2) disinfection of medical devices, including indwelling devices or implanted devices, and/or (3) disinfection of surgical sites. In some embodiments, the antimicrobial composition may comprise an antibiotic; nonetheless, in some embodiments, an antimicrobial composition of the present invention will display disinfecting properties without the inclusion of an antibiotic and it may be desirable to exclude antibiotics from the antimicrobial composition.

As shown in the below examples, in some aspects, antimicrobial compositions comprising a partially esterified polygalacturonic acid mixture and capyrlic acid that are formulated for topical administration are provided and may administered to a human patient (e.g., to treat a wound). As shown in the examples, the antimicrobial composition may be formulated as a non-antibiotic, antimicrobial wound ointment that may be used, e.g., to clinically treat biofilm in the chronic wounds. It is anticipated that the antimicrobial ointment will accelerate wound healing and may reduce the pain. Without wishing to be bound by any theory, data presented in the examples supports the idea that inclusion of the partially esterified polygalacturonic acid may contribute to the synergistic results with the fatty acid (e.g., caprylic acid) due to some interaction with the caprylic acid that may involve, e.g., improving the solubility of the fatty acid, providing emulsifying properties, and/or contributing to helping to maintain or buffer the acidic content of the antimicrobial composition.

An aspect of the present invention relates to an antimicrobial composition comprising: from about 0.5% to about 3% (w/w) of a polygalacturonic acid mixture and from greater than 0.1% to about 5% (w/w) of a $C_{6-12}$ fatty acid. The $C_{6-12}$ fatty acid may be a $C_{6-12}$ saturated fatty acid or a $C_{6-12}$ alkanoic acid. The $C_{6-12}$ fatty acid may be a $C_{6-10}$ saturated fatty acid or a $C_{6-10}$ alkanoic acid. The $C_{6-12}$ fatty acid may be hexanoic acid, octanoic acid, decanoic acid, dodecanoic acid, caprylic acid (octanoic acid), caproic acid, or lauric acid. In some embodiments, the $C_{6-12}$ fatty acid is caprylic acid (octanoic acid). In some embodiments, the composition comprises from about 0.2% to about 5%, from about 0.3% to about 5%, from about 0.4% to about 5%, or from about 0.4% to about 3% of the fatty acid. In some embodiments, the composition comprises from about 0.5%, 0.75%, 1%, 1.25%, 1.5%, 1.75%, 2%, 2.5%, 3%, or any range derivable therein (e.g., about 1%-3%), of the polygalacturonic acid. In some embodiments, the fatty acid is protonated or a free acid. The antimicrobial composition may have a pH of about 4.8 or less, about 3.7-4.8, or about 4-4.7. In some embodiments, the ratio of the polygalacturonic acid mixture consists of esterified polygalacturonic acid and de-esterified polygalacturonic acid in an amount of at least about 50% de-esterified polygalacturonic acid. In some embodiments, said amount is at least about 70% de-esterified polygalacturonic acid, wherein the de-esterified polygalacturonic acid is substantially deprotonated. In some embodiments, said amount is at least about 85% de-esterified polygalacturonic acid, wherein the de-esterified polygalacturonic acid is substantially deprotonated. The antimicrobial composition may further comprise a peroxide. In some embodiments, the peroxide is hydrogen peroxide. The hydrogen peroxide may be present in the antimicrobial composition in an amount of from about 0.1% to about 3%, or from about 0.1% to about 1%. The antimicrobial composition may further comprises one or more additional antimicrobial agent. The one or more additional antimicrobial agent may be an antibiotic, an antiseptic, chlorhexidine, gendine, gardine, silver, nanosilver, silver sulfadiazine, polyhexamethylene biguanide (PHMB), a chelator, a $C_{1-4}$ alcohol, a nitric oxide donor, a quarternary ammonium antimicrobial, or mixtures thereof. In some embodiments, the antimicrobial composition comprises the nitric oxide donor, and wherein the nitric oxide donor is a glyceryl nitrate, nitroprusside, nitrosoglutathione, a nitroso compound, nitrosothiol, nitrosocystein, nitrosoalbumin, nitro compounds, nitroaspiririn, isosorbide, diazeniumdiolate, nitrate, or nitrite. In some embodiments, the glyceryl nitrate is glyceryl trinitrate (GTN). In some embodiments, the antimicrobial composition comprises about 0.01-1% glyceryl trinitrate (GTN). The antibiotic is minocycline, rifampin, an aminoglycoside, quinolone, carbapenem, cephalosporin, glycopeptide, lipopeptide, lincosamide, macrolide, monobactam, nitrofuran, oxazolidinone, penicilin, polypeptide, sulfonamide, tetracycline, metronidazole, mucriprocin, anti-mycobacterial compound, or chloramphenicol. In some embodiments, the $C_{1-4}$ alcohol is ethanol. In some embodiments, the chelator is mercaptoethane sulfonate (MeSNA), citrate, EDTA, EDDS, or N-acetyl cysteine. In some embodiments, the antimicrobial composition further comprises an antibiotic; however, in other embodiments, the antimicrobial composition does not comprise an antibiotic. The antimicrobial composition may further comprise an analgesic agent, an antiscarring agent, an anti-inflammatory agent, an anticoagulant, a fragrance, a moisturizer, glycerol, a silicone compound, a vitamin, humectant, a polymer, a lubricant, a tactile agent, a thickener, a gelling agent, an emollient, a surfactant, an emulsifier, a moisturizer, a coloring or tinting agent, or a fragrance. The solution may comprise a pharmaceutically acceptable saline diluent. In some embodiments, the antimicrobial composition is further defined as a pharmaceutical composition or comprises a pharmaceutically acceptable excipient. The antimicrobial composition may comprise a protein such as, e.g., a gelatin, a plasticized gelatin (e.g., glycerol-gelatin), an alginate, a chitosan, collagen, or a proteoglycan (e.g., hyaluronic acid). In some embodiments, the antimicrobial composition is formulated for topical administration or administration to a wound. The antimicrobial composition may be formulated as an ointment, cream, spray, lotion, fluid, emulsion, suspension, microemusion, nanoemulsion, nanosuspension, or microsuspension. In some embodiments, the antimicrobial composition comprises a cellulose (e.g., carboxymethyl cellulose) and a glycerol (e.g., propylene glycol). In some embodiments, the antimicrobial composition comprises about 1-5% carboxymethyl cellulose and about 10-30% propylene glycol. In some embodiments, the antimicrobial composition comprises about 3% carboxymethyl cellulose and about 20% propylene glycol. In some embodiments, the antimicrobial composition comprises about 0.5-2% pectinic acid, about 0.3-0.5% caprylic acid, and about 0.01-1% glyceryl trinitrate (GTN). In some embodiments, the antimicrobial composition comprises about 1% pectinic acid, about 0.4% Caprylic acid, and about 0.03% glyceryl trinitrate (GTN). In some embodiments, the antimicrobial composition comprises about 1-1000 micrograms/ml glyceryl trinitrate and about 0.1-1% hydrogen peroxide. In some embodiments, the antimicrobial composition is further defined as a catheter lock or flush solution. In some embodiments, the composition comprises at least 0.75% or at least 1% of the polygalacturonic acid.

Another aspect of the present invention relates to a syringe, comprising a unit dose of a pharmacologically effective amount of an antimicrobial composition of the present invention or as described above.

Yet another aspect of the present invention relates to a vial, comprising a unit dose of a pharmacologically effective amount of an antimicrobial composition of the present invention or as described above.

Another aspect of the present invention relates to a medical device locking solution comprising or consisting of an antimicrobial composition of the present invention or as described above.

Yet another aspect of the present invention relates to a catheter comprising an antimicrobial composition of the present invention or as described above. The catheter may be a urinary catheter. In some embodiments, the urinary catheter is a double balloon catheter. In some embodiments, the urinary catheter is a Foley catheter, a double cuffed Foley catheter, or a Lerman Foley catheter.

Another aspect of the present invention relates to a method of disinfecting or cleaning a catheter in a subject, comprising administering an antimicrobial composition of the present invention or as described above to the catheter. The catheter may be an intravascular catheter, a urinary catheter, a brain catheter, a soaker catheter, a nephrostomy tube, or a drain or drainage catheter. In some embodiments, the catheter is a double balloon catheter, a single balloon catheter, a Foley catheter, or a Lerman Foley catheter. In some embodiments, the catheter is a urinary catheter and the method further comprises by flushing the antimicrobial composition between the urethra and external surface of the catheter. In some embodiments, the catheter comprises a proximal reservoir, and wherein the method further comprises filling the proximal reservoir with the antimicrobial composition. In some embodiments, the antimicrobial composition can drain along the exterior of the catheter shaft through one or more pores in the proximal reservoir. The proximal reservoir may be a cuff (e.g., an inflatable cuff). In some embodiments, the catheter comprises a distal reservoir. The distal reservoir may be a cuff (e.g., an inflatable cuff). In some embodiments, the method further comprises filling the distal reservoir with the antimicrobial solution. In some embodiments, the antimicrobial composition can drain along the exterior of the catheter shaft through one or more pores in the distal reservoir. In some embodiments, the catheter comprises three or more reservoirs or cuffs. The subject may be a human or a non-human animal such as, e.g., a mammal, a dog, a cat, a mouse, a primate, a monkey, an ape, a horse, a donkey, a pig, a sheep, a goat, or a cow. In some embodiments, the subject is a human.

Yet another aspect of the present invention relates to a composition for use in flushing or locking a catheter in a subject, wherein the composition is an antimicrobial composition of the present invention or as described above, and wherein the antimicrobial composition is further defined as a solution, an emulsion, or a suspension. The catheter may be an intravascular catheter, a urinary catheter, a brain catheter, a nephrostomy tube, or a drain or drainage catheter. In some embodiments, the catheter is a double balloon catheter, a Foley catheter, or a Lerman Foley catheter. In some embodiments, the subject is a human. In some embodiments, compositions and methods as described herein may be used for the treatment or disinfection of non-human animals, e.g., in a veterinary setting.

Another aspect of the present invention relates to a method of promoting wound healing or treating an infection in a subject, comprising administering an antimicrobial composition of the present invention or as described above to a wound or infection on or in the subject. In some embodiments, the antimicrobial composition is administered via a catheter, tube, canula, syringe, or soaker catheter. The antimicrobial composition may be formulated for topical administration. The subject may be a mammal such as, e.g., a dog, a cat, a mouse, a rat, a cow, a donkey, a pig, a sheep, or a horse. In some embodiments, the subject is a human.

Yet another aspect of the present invention relates to a composition for use in promoting wound healing in a subject, wherein the composition is an antimicrobial composition of the present invention or as described above.

Another aspect of the present invention relates to a method of treating a biofilm comprising contacting the biofilm with an antimicrobial composition of the present invention or as described above. The biofilm may comprise or consists of gram-positive bacteria, gram-negative bacteria, or fungi.

The pH of the antimicrobial composition may be present at or adjusted to a pH (e.g., a pH of about 4.8 or less) so that the fatty acid (e.g., the caprylic acid) is protonated or in a free acid state and/or the polygalacturonic acid (PG) is in an ionized (deprotonated) state. In some embodiments, the pH of the antimicrobial composition is about 3.5-4.8, more preferably about 3.7-4.8, or 3.5, 3.6, 3.7, 3.8, 3.9, 4, 4.1, 4.2, 4.3, 4.4, 4.5, 4.6, 4.7, 4.8, 4.9, 5.0 or any range derivable therein. In some embodiments, it is anticipated that it may be possible to adjust the antimicrobial formulation to a lower pH range (e.g., pH 2.0-3.5, pH 2.5-3.5) such that when the antimicrobial composition is applied in vivo (e.g., to a lower pH environment such as the digestive tract). In certain cases the pH may shift in situ from the lower pH range to a more alkaline pH range (e.g., pH 3.7-4.8). Generally, polygalacturonic acid (PG) has a pKa of about 3.7 (see Stoddart R W, Spires I P, Tipton K F., *Biochem J.* 1969 October; 114(4): 863-70. Solution properties of polygalacturonic acid); thus, at a pH above 3.5 the PG will be ionized (and not protonated). For example, in the pH range 3.7-4.8 the caprylic acid will be protonated but the PG will not be ionized (i.e., it will be deprotonated). Without wishing to be bound by any theory, the data provided herein supports the idea that when the antimicrobial composition comprises PG in an ionized (or deprotonated) state that this can help maintain the caprylic acid in the protonated state which may be necessary for its antimicrobial activity.

Polygalacturonic acid (e.g., a partially esterified polygalacturonic acid) in an antimicrobial composition as described herein may be a homopolymer of galacturonic acid but can also be heteropolymers of galacturonic acid, Rhamnose and other neutral sugars (such as arabinose, galactose and xylose); however, the majority of monomeric units in a polygalgcturonic acid are galacturonic acid. Some of the galacturonic acid units can be esterified, most commonly methoxylated but can also be ethoxylated (acylated), propoxylated and butoxylated etc. Some of the galacturonic acid units are free acids or protonated. The degree of esterification of partially esterified polygalacturonic acid can range from about 0.01-99.99%, more preferably less than about 80%, and even more preferably less than about 50%.

Some aspects of the present invention relate to antimicrobial compositions comprising a partially esterified polygalaturonic acid and a fatty acid. In some preferred embodiments, the fatty acid is a protonated fatty acid or a free acid. In some embodiments, the fatty acid is caprylic acid. One or more enhancer such as a peroxide and/or a nitric oxide donor (e.g., a glyceryl nitrate, glyceryl trinitrate (GTN)) can be included in the antimicrobial composition, e.g., to improve the speed of antimicrobial action. One or more chelators can also be included in the antimicrobial composition, e.g., to improve antimicrobial activity and/or maintain a desired local pH range. The chelators may be, e.g., MeSNA, a citrate, an EDTA, and/or an EDDS. In addition, thickeners, gelling agents, emollients, surfactants, emulsifiers, humectants, moisturizers, coloring or tinting agents and fragrances can be added to compositions of this invention to improve handling properties for specific applications.

Antimicrobial compositions as described herein may be used for a variety of purposes including, e.g., treatment of chronic wounds. For example, partially esterified polygalacturonic acid and fatty acids may be added to one or more thickening agents such as, e.g., methylcelluloses, hydroxymethylcelluloses, hydroxypropylmethylcelluloses and/or carboxymethylcelluloses which may help retain the composition in a wound and/or help absorb exudate. An ointment may further include a humectant such as propylene glycol. Without wishing to be bound by any theory, the humectant may facilitate contact with microbial biofilm present in wound beds and may help preserve a moist environment conducive to wound healing. The antimicrobial composition may further comprise an enhancer such as a nitric oxide donor and/or a peroxide, e.g., to accelerate biofilm eradication. In some embodiments, the antimicrobial composition further comprises one or more nitroprussides, nitrosoglutathiones, other nitroso compounds, nitrosothiols, nitrosocystein, nitrosoalbumin, nitro compounds, nitroaspirirns, isosorbides, diazeniumdiolates, nitrates and nitrites, a glyceryl nitrate, such as glyceryl trinitrate, and/or dilute hydrogen peroxide (e.g., less than about 1%, or 0.1, 0.2, 0.3, 0.4, 0.5, 0.6, 0.7, 0.8, 0.9% or any range derivable therein).

A variety of additional components may be included in an antimicrobial composition as described herein. For example, when it is desired to use the antimicrobial composition for skin disinfection, the polygalacturonic acid mixture and the fatty acid (e.g., caprylic acid) may be suspended in a volatile vehicle such as, e.g., water, an alcohol (e.g., ethanol, isopropyl alcohol), or a silicone which may allow application to skin but later evaporate, leaving antimicrobial components (e.g., the polygalacturonic acid mixture and the fatty acid) as a residue. In some embodiments, one or more emolients and/or surfactants may be included to improve tactile feel as can coloring or tinting agents. In some embodiments, the antimicrobial composition may be formulated as a low viscosity composition that can be sprayed (e.g., for application to skin or other surfaces). In some embodiments the antimicrobial composition can be delivered through an irrigation catheter, a soaker catheter, a cannula, a tube, a needle, or a trocar (e.g., to a surgical or other site with limited access). In some embodiments the antimicrobial composition can be formulated as a suppository, a hydrocolloid, particles, an emulsion, a suspension, a cream, or a paste. In some embodiments, the antimicrobial composition may be used for cleaning or disinfection of an indwelling or prosthetic medical device. These devices include catheters, tubes, stents, drains, dressings, shunts, pins etc. In some embodiments, the medical device is a urinary catheter such as a Foley catheters. Foley catheters typically consist of an open lumen through which urine can void and one or more inflatable cuffs. In some cases an inflatable cuff is present near the distal tip which resides distal to the urethral sphincter and when inflated retains the distal tip in the bladder. Inflation of cuffs is typically controlled by small lumens residing in the catheter wall. Foley catheters can frequently indwell for prolonged durations of longer than several days which increases the likelihood of microbial colonization and urinary tract infections. Antimicrobial compositions of the present invention may be instilled through the lumen into a draining cuff or reservoir from where they can drain along the shaft of the catheter in contact with the urethra. Thickeners and wetting agents such as, e.g., carboxymethylcellulose and/or propylene glycol may be included in the antimicrobial composition to control the rate of drainage and prolong contact times of the partially esterified polygalacturonic acid and fatty acids with the catheter. These approaches may be used, e.g., for treating, disinfecting, or eradicating a biofilm on the catheter or medical device. In another embodiment the medical device is a soaker catheter where antimicrobial compositions of the present invention can be instilled through the lumen and drain through the wall of the catheter to the external surfaces or contacting tissues. In yet another embodiment the medical device is a drainage tube where the antimicrobial compositions of the present invention can be instilled through a lumens and be conveyed to drain along the external surfaces through soaker pores or draining reservoirs.

Antimicrobial compositions as described herein may be pre-added to solid sponges or hydrogel matrices (e.g., for application or retention on surfaces such as skin or a medical device, catheter or prosthetic). The antimicrobial composition may comprise one or more of polyvinyl alcohol, hydrophilic polyurethanes, gelatin, collagen, chitosans, pectins, alginates and/or celluloses. Hydrogels may have higher affinity to water than other solvents (e.g., such as glycols) but may initially be loaded with a lower-affinity solvent which will be slowly displaced as water is absorbed. Hydrogel systems comprising a hydrogel matrix may be used release antimicrobial components from an antimicrobial composition of the present invention in the non-aqueous solvent as water is absorbed from the environment into the hydrogel matrix.

The duration of contact needed for disinfecting surfaces by fluid contact can vary by organism and/or by how well established a biofilm is being treated. As shown in the below examples, the inventors have found that biofilms can be eradicated within 2 hours by contact with compositions of low enough toxicity that they are suitable for use in intravascular devices.

Other physiologic surfaces which could be treated with the compositions disclosed here include, e.g., skin and wound beds, teeth, the oro and nasopharynx, surgical sites, organs, nerve tissue, tendons, cartilage and bone. In some embodiments, a solution of the present invention may be sprayed, nebulized, or inhaled by a subject into a lung, sinus, or respiratory tissue to treat or clean a wound or tissue, or reduce the growth of bacteria or fungi on the tissue. In some embodiments, a solution of the present invention may be administered topically to a subject, such as a human patient, to treat or prevent a sexually transmitted disease (STD). For contact with physiologic surfaces an antimicrobial composition of the present invention may be formulated into a gel, cream, or film, and the composition may include one or more coloring, aromatic, lubricious, moisturizing, pain relief and/or anti-inflammatory additive. Implanted medical device surfaces to which these compositions can be applied include, but are not limited to, catheters, cords, tubes, drains, shunts, stents, sutures, clips, staples, dressings, meshes, casings, etc. Environmentally exposed surfaces of plants, devices, buildings or machines can be treated with these compositions including surfaces in showers, locker-rooms, bathrooms and medical facilities. Surfaces of personal care and/or protection articles such as gloves, masks, respirators, patches, foot covers, shoe liners, flip flops, ear plugs, nose plugs etc. may be substantially disinfected with these compositions.

The antimicrobial compositions of the present invention may be contacted with a surface for a variety of periods of time to kill microorganisms or reduce the growth of microorganisms. For example, the contacting may be performed for at least 1, 2, 3, 4, 5 hours or at least 1, 2, 3, 4, 5 or more days, or 1, 2, 3, 4, 5 or more weeks, etc. In some embodiments, the contacting may be performed for less than 5, 4, 3, 2, or 1 hours, or less than 45, 30, or 15 minutes.

In addition to antimicrobial agents, an analgesic agent (e.g., lidocaine), an antiscarring agents (e.g., MeSNA), an anti-inflammatory agent (e.g., a steroid, a TNF alpha inhibitor, an aspirin, an ibuprofen, a cyclo-oxygenase inhibitor, a naproxen a non-steroidal anti-inflammatory agent), an anesthetic (e.g., a local anesthetic), or a pain-killer. In some embodiments, the antimicrobial composition comprises a leukotriene inhibitor such as, e.g., acitazanolast, iralukast, montelukast, pranlukast, verlukast, zafirlukast, and zileuton.

In some embodiments, an antimicrobial composition of the present invention does not contain an antibiotic. Nonetheless, in some embodiments, it may be desirable to include an antibiotic in an antimicrobial composition of the present invention. For example, an antimicrobial composition of the present invention may include member of the tetracycline group of antibiotics such as tigecycline, minocycline, doxycycline, or demeclocycline and/or analogs such as anhydrotetracycline, chlorotetracycline, or epioxytetracycline. In some embodiments, it is anticipated that a derivative of minocycline may be substituted for minocycline in various antimicrobial solutions or catheter lock solutions as described herein. In some embodiments, antimicrobial solutions or catheter lock solutions as described herein may include one or more additional antiviral agents and/or antifungal agents.

The antimicrobial composition may further comprises an antiseptic agent. Several antiseptic agents are known in the art and these include a taurinamide derivative, a phenol, a quaternary ammonium surfactant, a chlorine-containing agent, a quinaldinium, a lactone, a dye, a thiosemicarbazone, a quinone, a carbamate, urea, salicylamide, carbanilide, a guanide, an amidine, an imidazoline biocide, acetic acid, benzoic acid, sorbic acid, propionic acid, boric acid, dehydroacetic acid, sulfurous acid, vanillic acid, esters of p-hydroxybenzoic acid, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, N (5-nitro-2-furfurylidene)-1-amino-hydantoin, 5-nitro-2-furaldehyde semicarbazone, 3,4,4'-trichlorocarbanilide, 3,4',5-tribromosalicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecar-boxylic acid, 1,4-dihydro-1-ethyl-6-fluoro-4-oxo-7-(1-piperazinyl)-3-quinolinecarboxyli-c acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, or silver nitrate.

In some embodiments, the antimicrobial composition or composition may comprise a basic reagent and/or a dye. The basic reagent may be a guanidium compound, a biguanide, a bipyridine, a phenoxide antiseptic, an alkyl oxide, an aryl oxide, a thiol, a halide, an aliphatic amine, or an aromatic amine. In some specific aspects, the basic reagent is a guanidium compound. Non-limiting examples of guanidium compounds include chlorhexidine, alexidine, hexamidine, and polyhexamethylene biguanide (PHMB). In other specific embodiments, the basic reagent is a bipyridine. One example of a bipyridine is octenidine. In yet other aspects, the basic reagent is a phenoxide antiseptic.

The dye may be a triarylmethane dye, a monoazo dye, a diazo dye, an indigoid dye, a xanthene dye, an anthraquinone dye, a quinoline dye, an FD&C dye. Non-limiting examples of triarylmethane dye include gentian violet, crystal violet, ethyl violet, or brilliant green. Exemplary monoazo dyes inlude FD&C Yellow No. 5, or FD&C Yellow No. 6. Other non-limiting examples of FD&C dye include Blue No. 1 or Green No. 3. One non-limiting example of diazo dyes is D&C Red No. 17. An example of an indigoid dye is FD&C Blue No. 2. An example of a xanthene dye is FD&C Red No. 3; of an anthraquinone dye is D&C Green No. 6; and of an quinoline dye is D&C Yellow No. 1.

In some embodiments, an antimicrobial may contain one or more antiseptics. For examples, the antiseptic may be a phenoxide antiseptic (e.g., clofoctol, chloroxylenol or triclosan), gendine, genlenol, genlosan, or genfoctol.

Antimicrobial compositions and methods described herein can be used to reduce microbial agents (e.g., bacteria) from the surface of a medical device such as, e.g., a catheter, a drain, an endotracheal tube, a nephrostomy tube, a ventricular catheter or shunt, a biliary stent, an orthopedic device, a prosthetic valve, a medical implant, dental devices or dental implants, cardiac assist devices, vascular grafts, tracheostomy, ventriclulostomy devices, or intrathecal devices. In some aspects, the catheter is an indwelling catheter such as a central venous catheter, a peripheral intravenous catheter, an arterial catheter, a Swan-Ganz catheter, a hemodialysis catheter, an urinary catheter (e.g., a Foley catheter, a Lerman Foley catheter), a peritoneal catheter, an umbilical catheter, a percutaneous nontunneled silicone catheter, a cuffed tunneled central venous catheter or a subcutaneous central venous port. In some embodiments, the medical device is an endotracheal tube, a vascular catheter, a urinary catheter, a nephrostomy tube, a biliary stent, a peritoneal catheter, an epidural catheter, a central nervous system catheter, an intracranial catheter, an intraspinal catheter, an epidural catheter, an orthopedic device, a prosthetic valve, or a medical implant. The catheter may be a vascular catheter such as, e.g., a central venous catheter, an arterial line, a pulmonary artery catheter, and a peripheral venous catheter, an intraarterial catheter, or intravenous (i.v.) tubing.

In some embodiments, a pharmaceutical composition or catheter lock solution of the present invention may comprise a pharmaceutically acceptable excipient. The phrases "pharmaceutically acceptable" and "pharmacologically acceptable" refer to molecular entities and compositions that do not produce an adverse, allergic or other untoward reaction when administered to an animal, such as, for example, a human, as appropriate. The preparation of an pharmaceutical composition that contains an antimicrobial composition (e.g., a catheter lock solution, an ointment, a gel, a spray, a composition formulated for topical administration or administration to the skin or a wound, etc.) of the present invention and an additional active ingredient will be known to those of skill in the art in light of the present disclosure, as exemplified by *Remington: The Science and Practice of Pharmacy*, $21^{st}$ Ed., Lippincott Williams and Wilkins, 2005, incorporated herein by reference. Moreover, for animal (e.g., human) administration, it will be understood that preparations should typically meet sterility, pyrogenicity, general safety and purity standards as required by FDA Office of Biological Standards. In some embodiments, the antimicrobial composition may comprise one or more ingredient as described in U.S. Pat. Nos. 7,601,731, 5,362,754 and 5,688,516, which are incorporated by reference in their entirety without disclaimer. In some embodiments, an antimicrobial composition or catheter lock solution of the present invention may comprise one or more additional antiviral or antifungal agent.

Particular embodiments include a kit comprising an antimicrobial composition as disclosed herein, an absorbent element, a swab, an adhesive dressing, and a disposal bag; optionally, the kit may comprise a pair of gloves (e.g., sterile nitrile or latex gloves). In some embodiments, the kit is a care and maintenance kit for urinary (or other indwelling catheters) where a disinfecting liquid is packaged in a unit dose container for instillation (e.g. one or more syringes) and is combined with an absorbent element (such as a sponge or gauze described herein) in the kit to absorb any excess liquid that discharges at the proximal exit site of the device. In the case of a topical or wound ointment, the kit may include a wipe to clean the site, a swab or brush to spread the ointment, and an adhesive dressing to cover the site. In specific embodiments, the kit can also contain a disposal bag or container (including one suitable and marked for biohazardous disposal).

Certain embodiments include a catheter comprising: a first end and a second end; a central lumen extending from the first end and the second end; a catheter wall disposed around the central lumen, wherein the catheter wall comprises an outer surface; a first reservoir and a second reservoir; a first conduit in fluid communication with the first reservoir; a second conduit in fluid communication with the second reservoir; and a plurality of outlet ports in in the first reservoir.

Particular embodiments further comprise a first inlet port in fluid communication with the first conduit, and a second inlet port in fluid communication with the second conduit. In some embodiments the first conduit and the second conduit are in located within the catheter wall. In specific embodiments the plurality of outlet ports are arranged circumferentially around the outer surface of the catheter wall. Certain embodiments further comprise a first valve configured to control flow in the first conduit, and particular embodiments further comprise a second valve configured to control flow in the second conduit. Some embodiments further comprise an irrigation fluid container in fluid communication with the first conduit. In specific embodiments the irrigation fluid container is a first syringe, and in certain embodiments the irrigation fluid container is coupled to a pump.

In particular embodiments the irrigation fluid container comprises an antimicrobial composition as disclosed herein. In some embodiments the irrigation fluid container is configured to direct irrigation fluid through the first conduit and the plurality of outlet ports in the first reservoir. Specific embodiments further comprise a first inlet port in fluid communication with the first conduit, where the first inlet port is proximal to the first end. Certain embodiments further comprise an irrigation fluid container configured to direct irrigation fluid through the first inlet port, the first conduit and the plurality of outlet ports in the first reservoir.

Particular embodiments further comprise a pressure source in fluid communication with the second conduit, and in some embodiments the pressure source is a second syringe. In specific embodiments the pressure source is configured to inflate the second reservoir via the second conduit. Certain embodiments further comprise a second inlet port in fluid communication with the second conduit, wherein the second inlet port is proximal to the second end. In some embodiments the pressure source is configured to inflate the second reservoir via the second inlet port and the second conduit.

Other than reduction/eradication of microbes in medical devices, the flush solutions of the present invention are also useful in the eradication of the surfaces of other surfaces that microbes can grow on such as pipes, pipelines (e.g., an oil or water pipeline), ice machines, etc. In some embodiments, an antimicrobial composition of the present invention may be used for oral hygiene, e.g., as a mouthwash or for topical (skin) disinfection. In some embodiments, an antimicrobial composition of the present invention may be used with or included in or on a bandage, dressing (e.g., wound dressing), cast, suture, or staple. In some embodiments, an antimicrobial composition as described herein may be used to clean or disinfect a surface, or may be included on a sponge, gauze, a towel, or a wipe.

An "antimicrobial agent" is defined herein as an agent that has antibiotic properties against bacteria, fungi, viruses and other pathogens and includes antibacterial agents, antifungal agents, antiviral agents and antiseptic agents.

As used herein, the term "antifungal agent" is defined as a compound having either a fungicidal or fungistatic effect upon fungi contacted by the compound. As used herein, the term "fungicidal" is defined to mean having a destructive killing action upon fungi. As used herein, the term "fungistatic" is defined to mean having an inhibiting action upon the growth of fungi.

As used herein, the term "antibacterial agent" is defined as a compound having either a bactericidal or bacteriostatic effect upon bacteria contacted by the compound. As used herein, the term "bactericidal" is defined to mean having a destructive killing action upon bacteria. As used herein, the term "bacteriostatic" is defined to mean having an inhibiting action upon the growth of bacteria.

As used herein, the term "antiviral agent" is defined as a compound that can either kill viral agents or one that stops the replication of viruses upon contact by the compound.

For the purposes of this disclosure, the phrase "effective amount" or "therapeutically effective amount" is defined as a dosage sufficient to induce a microbicidal or microbistatic effect upon the microbes contacted by the composition on a surface.

As used herein the terms "contact", "contacted", and "contacting", or "exposed" and "exposure" are used to describe the process by which any of the antimicrobial compositions disclosed in the present invention, comes in contact with or direct juxtaposition with a surface of a medical device or any other surface from which microbial growth is to be reduced or eradicated.

As used herein in the specification, "a" or "an" may mean one or more. As used herein in the claim(s), when used in conjunction with the word "comprising", the words "a" or "an" may mean one or more than one. As used herein "another" may mean at least a second or more.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-C: Synergy of Polygalacturonic Acid and Caprylic Acid tested against MRSA (FIG. 1A), MDR-*Ps. aerugoinosa* (FIG. 1B), *Candida albicans* (FIG. 1C)

DESCRIPTION OF ILLUSTRATIVE EMBODIMENTS

Figure 2A:
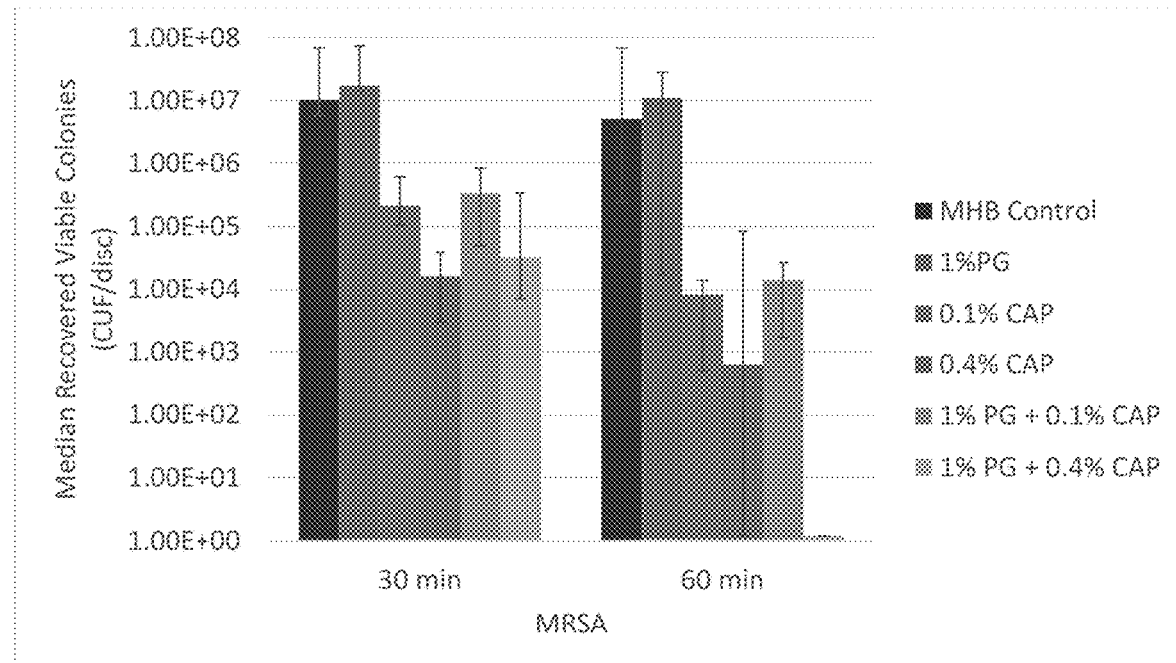
FIGS. 2A-C: Synergy of Polygalacturonic Acid and Caprylic Acid tested against MRSA (FIG. 2A), *Pseudomonas aerugoinosa* (FIG. 2B), *Candida albicans* (FIG. 2C) using the modified Kuhn's model, quantitative time-to-kill biofilm eradication model.

The present invention overcomes limitations in the prior art by providing improved antimicrobial compositions. In some aspects, the present invention is based, in part, on the observation that partially esterified polygalacturonic acid and caprylic acid can synergistically result in improved bacterial killing and antimicrobial properties. As shown in the below examples, partially esterified polygalacturonic acid or caprylic acid display very weak antimicrobial activity when administered alone; however, a synergistic and very strong antimicrobial activity was observed when these compounds are administered together. The antimicrobial compositions may be used in methods including, e.g., cleaning or disinfecting a medical device (e.g., a catheter), a prosthetic, a surface, skin, wound (e.g., as a lavage), or a surgical site.

In some embodiments, compositions of the present invention may be topically applied to the skin of a subject (e.g., a human patient) to treat an infection, e.g., that comprises a biofilm. Wounds in microbial contaminated environments can be difficult to heal due to the presence of biofilms. Biofilms are frequently present in chronic dermal wounds and contribute to their recalcitrance in healing (James et al., 2008). Staphylococcal biofilms have been reported to impair healing by delaying re-epithelialization of dermal wounds (Schierle et al., 2009). The increasing prevalence of antibiotic-resistant biofilms (US Department of Health and Human Services CfDCaP. Antibitoic Resistance Threats in the United States, 2013), impairs the efficacy of antibiotic wound therapies. We have developed a novel, non-antibiotic, antimicrobial wound ointment that is comprised of a combination of agents known to be safe if used topically on the skin. In vitro testing has shown the ointment to be highly effective in rapidly eradicating resistant gram positive, gram negative and fungal pathogens.

I. Definitions

The terms "antimicrobial medical device" and "medical device" as used herein, refer to an instrument, apparatus, implement, machine, contrivance, implant, or other similar or related article, including a component part, or accessory, which is subjected to sequential antimicrobial contact as described, and is intended for use in the diagnosis, treatment, and/or prevention of disease or other health-related condition in a subject. The subject can be any vertebrate, such as a mammal or a human. Non-limiting examples of antimicrobial medical devices include vascular catheters, such as peripherally insertable central venous catheters, dialysis catheters, long term tunneled central venous catheters, peripheral venous catheters, single-lumen and multiple-lumen short-term central venous catheters, arterial catheters, pulmonary artery Swan-Ganz catheters, and the like; urinary catheters, other long term urinary devices, tissue bonding urinary devices, renal stents, penile prostheses, vascular grafts, vascular access ports, wound drain tubes, hydrocephalus shunts, ventricular drainage catheters, neurologic and epidural catheters, neurostimulators, peritoneal dialysis catheters, pacemaker capsules, artificial urinary sphincters, small or temporary joint replacements, dilators, heart valves, orthopedic prosthesis, spinal hardware, surgical site repair mesh (e.g., hernia mesh), endotracheal tubes, biliary stents, gastrointestinal tubes, gloves (including latex, non-latex and nitrile), other medical garb, charts, bed rails, condoms, colorectal tract implants, male and female reproductive implants, cosmetic or reconstructive implants (e.g., breast, chin, cheek, buttock, nasal), medical device envelopes and pouches, including stethoscope drums, orthopedic implants (e.g., joint (knee, hip, elbow, shoulder, ankle), prostheses, external fixation pins, intramedullary rods and nails, spine implants), other medical and indwelling devices that may be subject to microbial infestation and/or activity; and metallic devices, such as cardiac pacemakers, defibrillators, electronic device leads, adaptors, lead extensions, implantable infusion devices, implantable pulse generators, implantable physiological monitoring devices, devices for locating an implantable pulse generator or implantable infusion device under the skin, and devices (e.g. refill needles and port access cannulae) for refilling an implantable infusion device. In some embodiments, antimicrobial compositions or solutions of the present invention may be used to substantially disinfect or reduce the growth of a microorganism (e.g., a bacteria of fungi) on a lumenal surface of a vascular catheter; for example the antimicrobial composition or solution may be used to flush the catheter and/or as a locking solution.

The term "antimicrobial agent", as used herein, refers to an agent, such as an antibiotic or an antiseptic, capable of preventing or reducing the growth or reproduction of a microorganism, such as a bacterial or fungal microorganism, or of killing a microorganism.

The term "bacterial and fungal organisms" as used in the present invention means all genuses and species of bacteria and fungi, including but not limited to all spherical, rod-shaped, and spiral bacteria. Non-limiting examples of bacteria include staphylococci (e.g., *Staphylococcus epidermidis, Staphylococcus aureus*), *Enterrococcus faecalis, Pseudomonas aeruginosa, Escherichia coli*, among other gram-positive bacteria and gram-negative bacilli. Non-limiting examples of fungal organisms include *Candida albicans* and *Candida krusei*.

II. Antimicrobial Compositions

In some aspects, the present disclosure provides compositions comprising polygalacturonic acid and caprylic acid. The composition (e.g., a aqueous composition, an ointment, etc.) may have an acidic pH such as, e.g., a pH of less than about 5. In some embodiments, the pH of the composition is from about 2 to about 5. In some embodiments, the pH is lower than 5. In some embodiments, the pH of the composition is from about 4 to about 4.5. In some embodiments, the composition is formulated in a buffer, such as an aqueous buffer. In some embodiments, the composition is formulated in a saline solution. The aqueous solution may be an isotonic 0.9% w/v saline solution. Other non-limiting examples of saline solutions which may be used are about 0.18%, 0.22%, 0.45%, 0.65%, 3%, 5%, 7%, or about 23.4% saline concentration. In some embodiments, the aqueous composition comprises a saline solution or a buffer solution which has been sterilized.

In some aspects, improved antimicrobial compositions that may be formulated as a wound ointment and include polygalacturonic acid and caprylic acid, optionally further comprising a nitric oxide donor (e.g., glyceryl trinitrate). As shown in the below examples, these compositions can display in vitro antimicrobial synergies, and these active ingredients are considered to be environmentally friendly green agents that are well known to have low toxicities towards humans. Previously the inventors have shown that the combination of glyceryl trinitrate (nitroglycerin), and the medium chain fatty acid, caprylic acid, can rapidly (within 2 hrs) eradicate biofilms of significant gram positive, gram negative and fungal biofilms (Rosenblatt et al., 2015). Without wishing to be bound by any theory, nitric oxide (donated by nitroglycerin) may accelerate wound healing by promoting angiogenesis, fibroblast migration and collagen deposition (Han et al., 2012). Nitroglycerin is widely used for treating hypertension in much higher doses than doses listed herein for wound treatment, and nitroglycerin may be administered through the skin (transdermally). Medium chain fatty acids (including caprylic acid) have been used in treating wounds in South America (Pieper and Caliri 2003). They are components included in skin creams and total parenteral nutrition formulations, and have been approved by FDA with GRAS (Generally Recognized as Safe) status. Glyceryl trinitrate (GTN) may be used in treating chronic infected gastrointestinal (GI) wounds. Wounds in the GI tract are complex to heal because these areas naturally contain high contents of microbial flora which can readily contaminate epithelial lesions. In 2011, the FDA approved Rectiv™ ointment (Actavis, Parsippany, NJ) which contains 0.4% GTN in a petrolatum base. Clinical trials showed that GTN ointment led to more rapid healing and reduced pain (Karanlik et al., 2009 and Fenton et al., 2006). The primary side effect was transient dose-related headache. Nitroglycerin-caprylic acid combination compositions presented in the below Examples reduces the GTN dose to less than $\frac{1}{10}^{th}$ of that in Rectiv™ ointment, and it is anticipated by the inventors that these reduced dosages presented herein may therefore significantly reduce or eliminate these dose-related side effects.

As shown herein and in the below Examples, the inventors have found that the combination of caprylic acid (CAP) and pectinic acid (PG) can display highly synergistic results in rapidly eradicating biofilm. Pectinic acid (also pectic or polygalacturonic acid) is naturally derived from fruit pectin, and is widely used in topical creams and other skin applications. It has been formally designated by FDA as GRAS [21CFR184.1588. Apr. 1, 2014] and can help maintain an acidic pH (4-4.5) in wound beds which is beneficial to wound healing.

A. Partially Esterified Polygalacturonic Acid

In some aspects, the present disclosure provides composition comprising a polygalacturonic acid (PG). Generally, esterified polygalacturonic acids have esterified carboxylic acid groups (e.g., esterified with an $alkyl_{(C1-6)}$ or a $cycloalkyl_{(C3-6)}$ group), and de-esterified polygalacturonic acids have carboxylic acids that are either in a deprotonated or protonated form. In some preferred embodiments, the antimicrobial composition comprises a partially esterified polygalacturonic acid in its ionized or deprotonated form.

Polygalacturonic acid (PG) can be naturally derived from pectin which is a structural biopolymer (polysaccharide) present in the cell walls of fruits and vegetables. Naturally derived PG is partially esterified (usually methoxylated), is usually derived from citrus rind or apple pomace and may contain minor components of other sugar molecules in its backbone (Sriamornsak 2013). The pK of PG varies with degree of esterification but ranges from about 3.5 to 4.1. At pHs above the pK, PG is usually soluble; however, at pHs below its pK it can form gels. The molecular weight of naturally derived PG is typically between 50 and 150 KDa (Sriamornsak 2013). PG is widely used in foods and is used in pharmaceutical tableting, coatings, in topical skin care products as a complex with Allantoin (Becker et al., 2010) as well as in wound healing products (Munarin et al., 2012). PG has been deemed Generally Rececognized as Safe (GRAS) by the FDA (Adminstration USFaD. Part 184, Section 1588, Pectins. In: Adminstration USFaD, ed. Code of Federal Regulations Title 21; 2015).

In some embodiments, the polygalacturonic acid (e.g., a de-esterified PGA or a partially esterified PGA) is a polymer further defined by the structure:

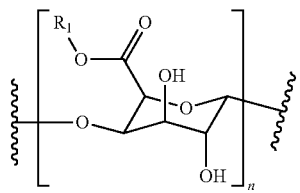

wherein: $R_1$ is hydrogen, $alkyl_{(C1-6)}$, substituted $alkyl_{(C1-6)}$, $cycloalkyl_{(C3-6)}$, or substituted $cycloalkyl_{(C3-6)}$. The polygalacturonic acids that may be used in the composition described herein may have a polymeric length of 3 to 1000 repeating units (n). In some embodiments, the number of repeating unit is from 10-750, 50-750, 50-500, of 100-500 repeating units. In some embodiments, a combination of polygalacturonic acids having a variety of polymer lengths (e.g., ranging from 3 to 1000 repeating units) may be included in an antimicrobial composition as described herein. In various embodiments, a polygalacturonic acid may be processed to produce increasing amounts of de-esterified polygalacturonic acid. The length of the polygalacturonic acid may be from about 50 to about 750 repeating units or from about 100 to about 500 repeating units. In some embodiments, the composition may comprise a polygalacturonic acid that is esterified at $R_1$ with an $alkyl_{(C1-6)}$ or substituted $alkyl_{(C1-6)}$; in some preferred embodiments, the composition comprises a ratio of (de-esterified polygalacturonic acid/esterified polygalacturonic acid) % of at least 50, 55, 60, 65, 70, 75, 80, 85, or 90 percent or higher or any range derivable therein of de-esterified polygalacturonic acid. In some embodiments, alkyl group at $R_1$ is methyl, ethyl, propyl, isopropyl, or butyl. In some aspects, the present disclosure provides polygalacturonic acid which has been esterified at some percentage of the $R_1$ positions; for example at least about 20, 25, 30, 35, 40, 45, 50, 55, 60, 65, 70, 75, 80, 85, or 90 percent or higher or any range derivable therein of these groups are in the de-esterified or protonated form, and the remaining carboxylic acid groups are esterified (e.g., esterified as methyl esters). In some embodiments, the percentage of the esterified carboxylic acid is from about 0.1% to about 75%, from 0.5% to about 50%, from about 0.5% to about 25%, or from about 1% to about 15%.

As used herein, the term "de-esterified polygalacturonic acid" refers to a polygalacturonic acid that has a carboxylic acid that is in a protonated or free acid form.

As used herein the term "partially esterified polygalacturonic acid" or a "polygalacturonic acid mixture" refers to a combination of both esterified polygalacturonic acid and de-esterified polygalacturonic acid. For example, the amount of de-esterified PGA may be at least 50, 55, 60, 65, 70, 75, 80, 85, 90, 95% or greater, or any range derivable therein.

In some aspects, the compositions of the present disclosure comprises from 0.5% to 10% of the polygalacturonic acid mixture (e.g., partially esterified polygalacturonic acid). The compositions may comprise from 0.5% to 5%, from 0.5% to 3%, from 0.5% to 2%, or about 1% of the polygalacturonic acid. In some embodiments, the composition comprises from about 0.25%, 0.5%, 0.75%, 1%, 1.25%, 1.5%, 1.75%, 2%, 2.5%, 3%, 3.5%, 4%, 4.5%, 5%, 6%, 7%, 8%, 9% to about 10%, or any range derivable therein. In some preferred embodiments, the polygalacturonic acid (e.g., partially esterified polygalacturonic acid) is in an ionic or deprotonated state.

B. Medium Chain Fatty Acids and Monoglycerides

Previously, the inventors have observed antimicrobial activity of caprylic acid and glyceryl trinitrate (GTN) as a novel non-antibiotic antimicrobial combination (Rosenblatt et al., 2013). Caprylic acid (CAP) is a medium chain fatty acid naturally present in human breast milk. CAP has been used intravenously in some total parenteral nutrition formulations (Wanten and Calder, 2007 and Rayyan et al., 2012). It is also readily absorbed following oral administration yielding significant blood concentrations (Haidukewych et al., 1982). Protonated CAP has been reported to have antimicrobial properties (Skrivanova and Marounek, 2007 and Yang et al., 2010). The pK of CAP has been reported as approximately 4.8 (CRC. *Handbook of Chemistry and Physics*. 85 ed. New York, N.Y.: CRC Press; 2004-2005).

In some aspects, the compositions described herein comprises one or more medium chain fatty acid or monoglyceride. In some embodiments, the fatty acid is a saturated fatty acid. A medium chain fatty acid or monoglyceride is a $C_6$-$C_{12}$ alkanoic acid or a glycerol ester of a $C_6$-$C_{12}$ alkanoic acid. Some non-limiting examples of medium chain fatty acids include caproic acid, caprylic acid, capric acid, or lauric acid. In some embodiments, the composition comprises caprylic acid. In some embodiments, the medium chain fatty acid (e.g., caprylic acid) is present in the antimicrobial composition in its protonated or free acid form In some aspects, the compositions described herein comprise at least 0.1% of the medium chain fatty acid or monoglyceride. The compositions that may be used in the present disclosure comprise from about 0.1% to about 5%, from about 0.1% to about 1%, or from about 0.1% to about 0.5% of the medium chain fatty acid or monoglyceride. In some embodiments, the amount of the medium chain fatty acid or monoglyceride is from about 0.1%, 0.15%, 0.2%, 0.25%, 0.3%, 0.35%, 0.4%, to about 0.5%, or any range derivable therein. The amount of the medium chain fatty acid or monoglyceride that may be used is about 0.1% or 0.4%.

In some aspects, the composition comprise both a medium chain fatty acid or monoglyceride and a polygalacturonic acid. In some embodiments, the amounts of each component when formulated together in a composition each comprise the amounts described above. In a non-limiting examples, the compositions may comprise from about from 0.5% to 10%, from 0.5% to 5%, from 0.5% to 3%, from 0.5% to 2%, or about 1% of the polygalacturonic acid and from about 0.1% to about 5%, from about 0.1% to about 1%, or from about 0.1% to about 0.5% of the medium chain fatty acid or monoglyceride.

The pH of the antimicrobial composition may be present at or adjusted to a pH (e.g., a pH of about 4.8 or less) so that the fatty acid (e.g., the caprylic acid) is protonated or in a free acid state. In some embodiments, the pH of the antimicrobial composition is about 3.5-4.8, more preferably about 3.7-4.8, or 3.5, 3.6, 3.7, 3.8, 3.9, 4, 4.1, 4.2, 4.3, 4.4, 4.5, 4.6, 4.7, 4.8, 4.9, 5.0 or any range derivable therein. In some preferred embodiments, the

C. Additional Antimicrobial Components

In some aspects, the present composition further comprises another antimicrobial component such as a nitric oxide donor, an alcohol, and/or a peroxide. Some non-limiting examples of these antimicrobial components include hydrogen peroxide, magnesium, calcium, strontium, barium, lithium, potassium, sodium peroxide, glyceryl trinitrate, isosorbide mononitrate, pentaerythrityl tetranitrate, S-nitrosoglutathione, S-nitroso-N-acetylpenicillamine, S-nitroso-captopril, sodium nitroprusside, S-nitroso-N-valerylpenicillamine, spermine NONOate, an essential oil, or ethanol.

Antimicrobial compositions composition comprise about 0.01%-10%, about 0.1%-10%, about 0.1% to about 5%, from about 0.01% to 0.1%, from about 0.01% to about 0.05%, from about 0.1% to about 1%, from about 0.1% to about 0.5%, or about 0.01%, 0.02%, 0.03%, 0.04%, 0.05%, 0.1%, 0.2%, 0.3%, 0.4%, 0.5%, 0.75%, 1%, 2%, 3%, 4%, 5%, or any range derivable therein of the additional antimicrobial component, such as a peroxide and/or a nitric oxide donor. For example, an antimicrobial composition comprising the polygalacturonic acid and the fatty acid may further comprise about 0.1-2% (e.g., 0.3%) hydrogen peroxide, glyceryl trinitrate (e.g., at a concentration of about 0.05-1500, 1-1000, or 10-500 micrograms/ml), and/or a chelator (e.g., citrate, MeSNA, EDTA, disulfiram; for example, at a concentration of about 0.1-10%, or 1%, 2%, 3%, 4%, 5%, 6%, or 7% (v/v) or any range derivable therein).

In some embodiments, a glyceryl nitrate (e.g., glyceryl trinitrate, glyceryl dinitrate, glyceryl mononitrate) may be present in an antimicrobial composition or solution of the present invention in an amount of about 0.05-2000, 0.1-2000, 0.1-1750, 0.1-1500, 0.1-1250, 0.1-1000, 1-1000, 10-500, 25-500, 25-250, 50-500, 75-150, or about 10, 20, 30, 40, 50, 60, 70, 80, 90, 100, 110, 120, 130, 140, 150, 160, 170, 180, 190, or 200 micrograms/ml, or any range derivable therein. In some embodiments, intermediate concentrations such as, e.g., 11, 12.5, etc. are contemplated. For example, the concentration of the glyceryl nitrate may be greater than about 10, 11, 12, 13, 14, 15, 20, or 25 micrograms/ml. In some embodiments, the glyceryl nitrate may be in a concentration less than about 2000, 1750, 1500 micrograms/ml. In some embodiments, about 50-125 or about 100 micrograms/ml glyceryl nitrate may be included in a antimicrobial composition (e.g., a catheter locking solution, spray, cream, ointment, preparation for topical application to the skin or a wound, etc.) as these concentrations can be safely used clinically. In some preferred embodiments, the glyceryl nitrate is GTN.

Glyceryl nitrates include mono-, di-, or trinitrates (e.g., glyceryl mononitrate, glyceryl dinitrate, or glyeryl trinitrate). Mixtures of glyceryl mononitrate, glyceryl dinitrate, and/or glyeryl trinitrate may be used in various embodiments of the present invention. GTN is also referred to as nitroglycerin, nitroglycerine, trinitroglycerin, trinitroglycerine, 1,2,3-trinitroxypropane, and glyceryl trinitrate.

A variety of chelators may be used with the present invention. For example, the chelator may be citrate, a tetra acetic acid, an EDTA, a thiosulfate, N-acetyl cysteine, disulfiram, a hydroxy acid, a hydroxamic acid, ethylene diaminedisuccinate (EDDS), Tetrakis hydroxymethyl phosphonium sulfate (THPF), or MesNA. The chelator may be citrate. The chelator may be ethylene diaminedisuccinate (EDDS) or Tetrakis hydroxymethyl phosphonium sulfate (THPF). In some embodiments, the chelator is a hydroxy acid, such as an α-hydroxy acid. The hydroxy acid may be lactic acid, gluconic acid, glycolic acid, galacturonic acid, salicylic acid, or glucaronic acid. In some embodiments, the chelator is a hydroxamic acid. The hydroxamic acid may be hydroxamic acid, benzohydroxamic acid, salicylhydroxamic acid, or suberoylanilide hydroxamic acid (SAHA). The chelator may be, e.g., EDTA free acid, EDTA 2Na, EDTA 3Na, EDTA 4Na, EDTA 2K, EDTA 2Li, EDTA 2NH$_4$, EDTA 3K, Ba(II)-EDTA, Ca(II)-EDTA, Co(II)-EDTACu (II)-EDTA, Dy(III)-EDTA, Eu(III)-EDTA, Fe(III)-EDTA, In(III-EDTA, La(III)-EDTA, CyDTA, DHEG, diethylenetriamine penta acetic acid (DTPA), DTPA-OH, EDDA, EDDP, EDDPO, EDTA-OH, EDTPO, EGTA, HBED, HDTA, HIDA, IDA, Methyl-EDTA, NTA, NTP, NTPO, O-Bistren, TTHA, EGTA, DMSA, deferoxamine, dimercaprol, zinc citrate, a combination of bismuth and citrate, penicillamine, succimer or Etidronate. It is contemplated that a chelator which binds barium, calcium, cerium, cobalt, copper, iron, magnesium, manganese, nickel, strontium, or zinc may be included in various embodiments of the present invention.

The antimicrobial composition may comprise an alcohol. For example, the antimicrobial composition may comprise a $C_{1-4}$ alcohol at a concentration of about 1-30%, 2.5-25%, 5-25%, 5-15%, 10-15%, 5-10%, 10-30%, 10%, 15%, 20%, 25%, 30%, 35%, 40%, 45% or any range derivable therein (e.g., in a catheter flush or lock solution, an ointment, cream, spray, solution, etc.). The $C_{1-4}$ alcohol may be ethanol, isopropanol, methanol, or butanol. In some preferred embodiments, the $C_{1-4}$ alcohol is ethanol or isopropanol. In some embodiments, the alcohol may be cyclohexanol, benzyl alcohol, chlorobutanol, 2-bromo-2-nitropropan-1,3-diol, or phenylethyl alcohol. In some embodiments, higher concentrations of an alcohol (e.g., greater than 50%) may be used in various embodiments, e.g., on the surface of a device or prosthetic or where the alcohol may be reasonably tolerated by a subject (e.g., when used for application to the skin. Nonetheless, in some embodiments, lower concentrations of an alcohol may be preferable since little or no irritation may result from lower concentrations of alcohol (e.g., when used as a catheter lock or flush solution).

In some embodiments, an antimicrobial composition of the present invention does not include an antibiotic; for example, antibiotic resistance has emerged as a problem in clinical settings, and in some embodiments it may be beneficial to exclude an antibiotic from an antimicrobial composition of the present invention. Nonetheless, in some embodiments, it may be desirable to include one or more antibiotics in an antimicrobial composition of the present invention. A variety of antibiotics may be used with the present invention. In some embodiments, the antibiotic is trimethoprim and/or minocycline. For example, one or more antibiotic agent(s) may be included in an antimicrobial composition of the present invention, such as, e g, aminoglycosides, beta lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymxins, lipo-peptide antibiotics, as well as pharmacologically acceptable sodium salts, pharmacologically acceptable calcium salts, pharmacologically acceptable potassium salts, lipid formulations, derivatives and/or analogs of the above. The antibiotic may be a member of the penicillin group of antibiotics such as, e.g., amoxicillin, ampicillin, benzathine penicillin G, carbenicillin, cloxacillin, dicloxacillin, piperacillin, or ticarcillin, etc. Examples of cephalosporins include ceftiofur, ceftiofur sodium, cefazolin, cefaclor, ceftibuten, ceftizoxime, cefoperazone, cefuroxime, cefprozil, ceftazidime, cefotaxime, cefadroxil, cephalexin, cefamandole, cefepime, cefdinir, cefriaxone, cefixime, cefpodoximeproxetil, cephapirin, cefoxitin, cefotetan etc. Examples of beta lactamase inhibitors include clavulanate, sulbactam, or tazobactam. The antibiotic may be a macrolide such as, e.g., erythromycin, azithromycin, or clarithromycin. Examples of quinolones and fluoroquinolones that may be used include nalidixic acid, cinoxacin, trovafloxacin, ofloxacin, levofloxacin, grepafloxacin, trovafloxacin, sparfloxacin, norfloxacin, ciprofloxacin, moxifloxacin and gatifloxacin. Examples of sulphonamides that may be used include mafenide, sulfisoxazole, sulfamethoxazole, and sulfadiazine. The streptogramin class of antibacterial agents is exemplified by quinupristin, dalfopristin or the combination of two streptogramins. Drugs of the rifamycin class typically inhibit DNA-dependent RNA polymerase, leading to suppression of RNA synthesis and have a very broad spectrum of activity against most gram-positive and gram-negative bacteria including *Pseudomonas aeruginosa* and *Mycobacterium* species. An exemplary rifamycin is rifampicin. Other antibacterial drugs are glycopeptides such as vancomycin, teicoplanin and derivatives thereof. Yet other antibacterial drugs are the polymyxins which are exemplified by colistin. In addition to these several other antibacterial agents such as prestinomycin, chloramphenicol, trimethoprim, fusidic acid, metronidazole, bacitracin, spectinomycin, nitrofurantion, daptomycin or other leptopeptides, oritavancin, dalbavancin, ramoplamin, ketolide etc. may be used in preparing the compositions described herein.

It is also contemplated that any additional pharmacologically active ingredients or sterilization agents may be included in an antimicrobial composition of the present invention or may be used in combination with an antimicrobial composition of the present invention to further reduce or eliminate pathogenic microbes and viruses. Typical pharmacologically active ingredients include antifibrin agents, anti-thrombotic agents, and anti-inflammatory agents. Anti-inflammatory agents include steroids, and nonsteroidal anti-inflammatory agents, and salicylates. Antithrombotic drugs include acetylsalicylic acid, dipyridamole, heparin, ibuprofen, indomethacin, prostaglandins, sulfinpyrazone, warfarin, thrombolytic enzymes such as streptokinase, urokinase, or plasminogen activator. Complexing agents such as ammonium-1-pyrrolidine dithiocarbanate may also be used. However, the above examples are not meant to be limiting. In some embodiments, an antimicrobial composition as described herein may comprise one or more additional anticoagulant and/or an anti-inflammatory agent.

An antimicrobial compositions of the present invention (e.g., an antimicrobial solution, ointment, cream, spray, solution, catheter lock or flush solution) as described herein, may contain an additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. An antimicrobial composition as described herein may contain an additional active ingredient, e.g., as exemplified by *Remington: The Science and Practice of Pharmacy, 21$^{st}$ Ed.*, Lippincott Williams and Wilkins, 2005, incorporated herein by reference. Moreover, for animal (e.g., human) administration, it will be understood that preparations should typically meet sterility, pyrogenicity, general safety and purity standards as required by FDA Office of Biological Standards.

III. Cleaning or Disinfecting Medical Devices

In addition to use with catheters (e.g., as a catheter lock solution or a catheter flush solution), an antimicrobial composition or solution of the present invention may be applied to or used with a medical device. In some embodiments, the antimicrobial composition is used as a catheter lock solution, e.g., with a Foley catheter, a Lerman Foley catheter, or a double balloon catheter.

The medical device may be, e.g., an endotracheal tube, a nephrostomy tube, a feeding tube, a gastric tube, a nasal tube, a biliary stent, an orthopedic device, a valve, a prosthetic valve, a drainage tube, a drain, a shunt, a staple, a clip, a mesh, a film, a blood exchanging device, a port, a cardiovascular device, a defibrillator, a pacemaker lead, a wire coating, an ocular implant, an auditory implant, a cochlear implant, a dental implant, a stimulator, a drug delivery depot, a filter, a membrane, a vascular access port, a stent, an envelope, a bag, a sleeve, intravenous or other tubing, a bag, a dressing, a patch, a fiber, a pin, a vascular graft, a suture, a cardiovascular suture, or an implantable prosthesis. In some embodiments, the medical device is a catheter such as, e.g., a vascular catheter, a urinary catheter, an intracranial catheter, an intraspinal catheter, a peritoneal catheter, a central nervous system catheter, a cardiovascular catheter, a drainage catheter, a soaker catheter, an aspirating catheter, an intrathecal catheter, a neural catheter, a vaginal catheter or tube, a uterine catheter or tube, a stimulating catheter, or an epidural catheter. The catheter may be a vascular catheter such as, e.g., a central venous catheter, an arterial line, an pulmonary artery catheter, a peripheral venous catheter, an intravenous catheter, or an intraarterial catheter.

Medical devices that are amenable to treatment according to a method of the present invention generally include non-metallic materials, such as rubber, plastic, polyethylene, polypropylene, polyurethane, silicone, polytetrafluoroethylene (PTFE), polyethylene terephthalate (PET), latex, nitrile, and other polymeric and elastomeric materials (e.g., collagens, gelatins, crosslinked collagens, crosslinked gelatins, hyaluronates, chitosams, alginates, allografts, xenografts, autografts), as well as metals, such as titanium, and metal alloys, such as stainless steel and nitinol. Those skilled in the art will appreciate that the listing of non-metals, metals, and metal alloys as described herein is exemplary only, and is not intended to be exclusive. Other materials that are amenable to treatment as described herein are also within the scope of the present invention.

In some embodiments, an antimicrobial composition is used to clean or rinse a medical device. Nonetheless, in some embodiments, the medical device may be washed following contact with the antimicrobial composition.

Additional details regarding contacting an antimicrobial with a medical device not specifically recited herein can be found, e.g., in U.S. Pat. Nos. 5,217,493, 5,624,704, 5,902,283, and 7,651,661, as well as in U.S. Patent App. Pub. Nos. 2005/0197634, 2003/0078242, 2007/0154621, 2008/0183152, 2010/0055086, 2011/0201692, and 2012/0064372 all incorporated by reference.

Figure 5:
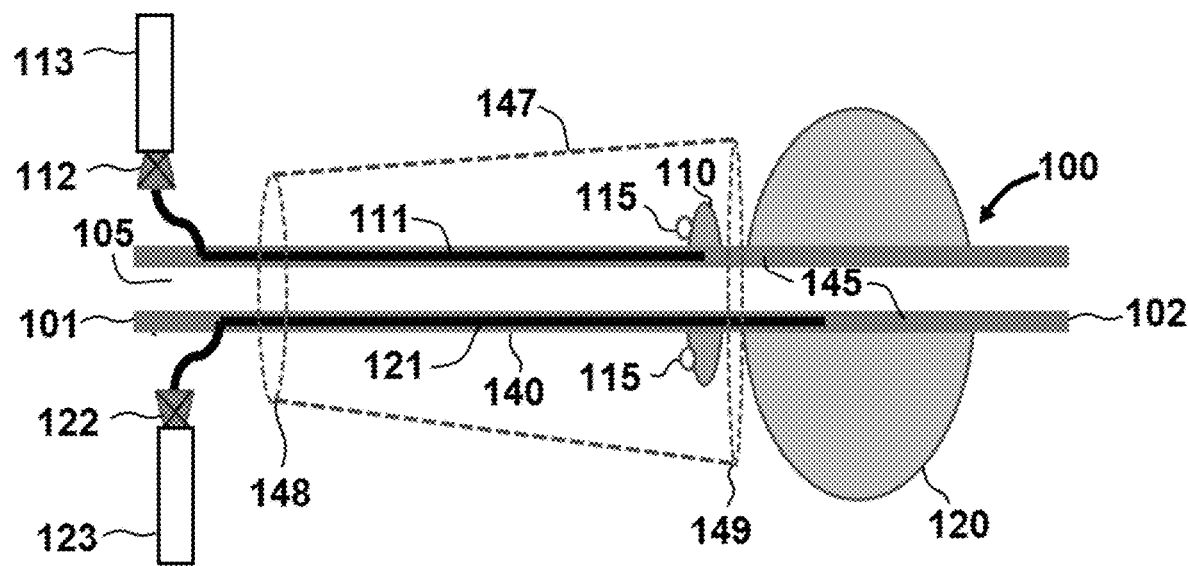
FIG. 5: A schematic drawing of a catheter according to exemplary embodiments of the present disclosure.

Referring now to FIG. 5, an exemplary embodiment is shown of a drainage device that can be used in conjunction with the antimicrobial compositions disclosed herein. In this embodiment, the drainage device is configured as a catheter 100. In particular embodiments, catheter 100 may be configured as a urinary catheter comprising a first end 101 (e.g. a proximal end close to a urine collection container) and a second end 102 (e.g. a distal end extending into the bladder). Catheter 100 comprises a central lumen 105 that extends between proximal end 101 and distal end 102 and allows for fluid to be drained from the bladder (or other location within the body) to the collection container.

In the embodiment shown, catheter 100 also comprises a proximal reservoir 110 and a distal reservoir 120. In certain embodiments, proximal reservoir 110 may be an irrigation cuff and distal reservoir 120 may be a retention cuff. A first conduit 111 and inlet port 112 are in fluid communication with proximal reservoir 110, while a second conduit 121 and inlet port 122 are in fluid communication with distal reservoir 120. In this embodiment, inlet ports 112 and 122 are located proximal to first end 101 to allow a user to direct fluids (including liquids or gas, such as air) through first and second conduits 111 and 121. In certain embodiments, inlet ports 112 and 122 may each comprise a valve that can be opened or closed to control flow.

For example, a user can couple an irrigation fluid container 113 (e.g., a syringe) to inlet port 112 and open inlet port 112 during or after the insertion of catheter 100. The irrigation fluid can be directed through conduit 111 toward second end 102 and into proximal reservoir 110 of catheter 100. Proximal reservoir 110 comprises outlet ports 115 (e.g. openings in the reservoir such as holes or slits) configured to dispense irrigation fluid from proximal reservoir 110.

When catheter 100 inserted to the desired depth, a user can couple a pressure source 123 (e.g., a syringe or other suitable device) to inlet port 122, which can then be opened to inflate distal reservoir 120 via conduit 121. In certain embodiments, inlet port 122 may comprise a valve that can be opened or closed to control the inflation of distal reservoir 120. When inflated, distal reservoir 120 can retain second end 102 of catheter 100 in the bladder.

In exemplary embodiments, the irrigation fluid directed through conduit 121 may comprise an antimicrobial composition as disclosed herein. In specific embodiments, the irrigation fluid may comprise synergistic antimicrobial compositions with low toxicities comprising partially esterified polygalacturonic acid and fatty acids that could be applied to disinfect tissues or surfaces of catheter 100. In particular embodiments, the irrigation fluid could be intermittently applied in situ to irrigate the external surface of catheter 100 in contact with the urethra 147.

In other embodiments, different types of devices may be used in conjunction with the irrigation fluid, including for example, drainage devices comprising surgical drains, drainage catheters such as nephrostomy tubes, shunts and catheters such as urinary catheters. Exemplary drainage devices comprise at least one lumen that can conduct fluid from a cavity, organ or tissue inside of the body to a collection container outside of the body. The collection container can be a bag or vessel, an absorbent medium or could be returned to another part of the body.

In general, drainage through central lumen 105 occurs passively (without applied pressure or suction), but active drainage can occur through application of pressure, squeezing or other forces or by suction. Catheter 100, in addition to having one or more lumens, also has at least one wall 145 (disposed around central lumen 105) with an outer surface 140. Outer surface 140 may not directly contact the draining fluid through central lumen 105.

Outer surface 140, however, is in contact with tissues or conduits until it traverses the skin to outside of the body where it typically connects to a bag, reservoir or absorbent medium. Outer surface 140 can cause irritation if it rubs against tissues it passes through. Outer surface 140 can also become colonized by pathogenic microbes and can therefore be a source of infection. The ability to irrigate outer surface 140 with medicated, lubricious or adhesive fluids via outlet ports 115 can therefore be beneficial. In some cases the medicated fluid can be disinfecting and additionally can contain other medications such as pain relievers, antifibrotic or mucolytic medications, or collagenolytic agents (to treat strictures for example), and in some embodiments the medicated fluid may optionally include one or more fragrances to mask odors. Of particular interest are the antimicrobial compositions as disclosed herein.

For the case where catheter 100 is a urinary catheter, outer surface 140 would contact the surface tissues of urethra 147. The irrigating fluid would then reside between outer surface 140 and urethra 147. A lubricious fluid could help reduce urethral mechanical trauma and an antimicrobial fluid could prevent microbes from colonizing the external surface of the urinary catheter into the bladder and beyond.

The urethra is distensible when pressure is applied but typically is in a collapsed resting state. When a urinary drainage catheter is inserted, the urethra will normally collapse around the external surfaces of the catheter. In order to irrigate the urethra, a pressure gradient directed from urethral-bladder 149 junction towards meatus 148 is preferred. Irrigation fluid can then flow down the pressure gradient between urethra 147 and external surface 140 of catheter 105 until it exits at meatus 148. Meanwhile, the urinary drainage function is performed by central lumen 105, which provides a conduit from the bladder to outside of the body.

In the embodiment shown in FIG. 5, distal reservoir 120 can be configured as a retention cuff or balloon to secure catheter 100 near the drainage entry point following insertion. Other securement means inside the body near the drainage entry point are also possible including, clips, springs, string, bands, prongs, staples, glues, adhesives etc. Drainage catheters can also be secured the exit site, although if not also secured at the drainage entry point, a risk of migration of the tip of the drainage catheter exists. The external surface irrigation devices described herein can work with any suitable securement means.

In certain embodiments, catheter 105 may configured similar to a Foley catheter where distal reservoir 120 is configured as a securement balloon. With this configuration, the securement balloon is below the tip and can be inflated such that central lumen 105 is unaffected. The inflated balloon surface can extend outward from outer surface 140. In certain embodiments, lumen 121 can be embedded in wall 145 of catheter 105. Catheter 105 can be inserted in a deflated state and is inflated only when the distal end 102 has been inserted into the bladder. The diameter of the distal reservoir 120 is larger than the diameter of the urethral bladder junction so that distal end 102 is maintained in the bladder by the physical entrapment of the inflated distal reservoir 120 (e.g. cuff) at urethral bladder junction 149. In certain embodiments, catheter 100 may have an additional balloon or cuff at the tip in the bladder to reduce trauma from the tip to the bladder wall.

In certain embodiments of catheter 105, proximal reservoir 110 is configured as balloon just below urethral bladder junction 149. In one embodiment, the balloon is comprised of an elastomeric material. Silicone, latex, nitrile, urethane or fluoroelastomers are examples of materials from which proximal reservoir 110 can be made. In certain embodiments outlet ports 115 (e.g. holes or slits) at its proximal base directed down the shaft towards the meatus.

Outlet ports 115 can be arranged circumferentially at the base of the proximal reservoir 110 so as to distribute irrigating fluid uniformly around outer surface 140 of catheter 105. As previously described, irrigation fluid can injected into proximal reservoir 110 through inlet port 112 using irrigation fluid container 113 (e.g. a syringe) that can pump fluid under positive pressure. Inflating proximal reservoir 110 with pressurized fluid causes it to temporarily expand. In certain embodiments, there is a one-way valve between the inlet port 112 and irrigation fluid container 113 preventing backflow. The expanded proximal reservoir (e.g. irrigation cuff) pushes on the fluid forcing it through outlet ports 115 at the base of the cuff. Over time, the pressure is relieved as the irrigating fluid is pumped down urethra 147 towards meatus 148.

In exemplary embodiments, first reservoir 110 (e.g. the irrigation cuff) can be molded and bonded to the shaft of catheter 100 above and below where outlet ports 115 exit the catheter wall 145 to outer surface 140. In certain embodiments, the holes or slits can be pre-formed prior to adhering to the shaft or can be formed by inflating the cuff with a fluid, changing the temperature to freeze or gel the fluid to a solid, poking the holes with the solidified inflation fluid and then warming up to where the inflating fluid liquefies and exits the system. An example of such an inflation fluid is a gelatin solution, where the fluid is instilled at a temperature above 40 degrees Celsius to inflate the irrigation cuff, taken to refrigeration at 4 degrees Celsius where the fluid solidified, holes are poked at the base of the irrigation cuff in the solidified state and the assembly is reheated to near 40 degrees Celsius and the gelatin solution is evacuated and flushed out.

The irrigation cuff and/or outlet ports can be fitted with nozzles or directional elements that facilitate spraying or directional discharge of the irrigating solution under pressure. The irrigation cuff can also be fitted with miniature valves that can be actuated remotely for delayed or pulsatile discharge of the irrigating fluid into the space between the urethra and outer wall of the drainage catheter. A pump can be connected to the inflation valve of the irrigation in order to provide programmed intermittent or continuous urethral irrigation.

A disposable absorbent element can be secured at meatus 148 to collect irrigating fluid discharged at the meatus along outer surface 140 of catheter 100. Examples of absorbent elements are sponges, superabsorbent hydrophilic polymers, fleeces, fabrics, or gauzes. A ribbon of gauze can be tied around the external catheter surface proximal to meatus 148 and slid up to contact meatus 148. A gauze can also have an adhesive backing or adhesive tabs that can be used to secure it around the external surface of the catheter at the meatus. The adhesive backing or tabs can have pre-cut perforations that make it easy to tear for removal. Similarly, an absorbent sponge (such as a natural, urethane or polyvinylalcohol based sponge) can be secured around outer surface 140 either with adhesive tabs or backing or by preforming to an annular shape with that can form a compression fit around outer surface 140 of catheter 100. The absorbent element can also be a strip or film made from superabsorbent polymers or can be in granule form. Single piece annular absorbent elements can contain slits that allow them to be slid over external surfaces of catheters.

In certain embodiments, either a fabric, a film or a sponge can also be secured using magnets that can hold it together as well as to catheter 100. The catheter, for example could have a magnetic band at meatus 148 which can help secure and adhere the absorbent element or two, half-donut shaped elements can be magnetically secured around the catheter shaft. Velcro or clips can also be used to secure the absorbent element. Velcro tabs or clips can be built in to the absorbent element or can be wrapped around it and then compressed to secure it. Securement can also be accomplished by the unidirectional ratcheting action of "cable tie" type connectors, harpoon/receiver and similar clamps, prongs with latches and receivers, hooks cords, lanyards, fasteners, twist locks, ties and tie-downs. The securement clips or ties can be pre-scored to be readily broken apart when desired for removal.

In some embodiments, an elastomeric, or firm, cup-shaped concave collector can also be secured around outer surface 140 of catheter 100 with absorbent material contained within the cup collection space. The absorbent element can also have outward-facing convex protrusions which might be useful for certain anatomies. Disposable absorbent elements can be packaged and sold together with irrigation containers such as syringe in single-use, disposable, catheter external surface care and maintenance kits. The irrigation can be performed daily, or multiple times daily with frequency varied as needed.

One type of irrigation fluid contains the antimicrobial compounds caprylic acid and polygalacturonic acid described herein. It may also contain enhancers such as hydrogen peroxide or nitric oxide donors (like nitroprussides or nitroglycerin). The irrigation fluid may also contain viscosity modifying compounds such as thickening agents. The irrigation fluid can contain components that protect urethral tissues. One combination is Carboxymethylcellulose and propylene glycol. The irrigation fluid can be either aqueous-based, lipid-based, polymer-based, or inorganic. The irrigation fluid can also deliver MeSNA, N-acetylcystein, or collagenolytic agents to alleviate strictures that might form over extended catheterizations. Similarly, clotting agents for torn urethras and pain-relieving agents such as aspirin or lidocaine can be included in the irrigation fluid.

IV. Antimicrobial Agents and Microbes

Antimicrobial compositions of the present invention may be used to kill, destroy, or reduce the proliferation of a variety of microbes. Some non-limiting exemplary bacterial and fungal microbes that can be reduced or eradicated by the compositions and methods of the invention include *Staphyloccous* species (such as *Staphylococcus epidermidis*), *Staphylococcus aureus; Asperigllus* species (such as *Aspergillus flavus, Aspergillus terreus*), *Enterrococcus faecalis, Pseudomonas aeruginosa, Escherichia coli, Fusarium oxysporum*, and *Candida* species (such as *Candida krusei, Candida parapsilosis, Candida tropicalis, Candida albicans* and *Candida glabrata*).

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Synergistic Caprylic and Polygalacturonic Acid Combinations for Eradication of Biofilm There is a need in contaminated dermal and epithelial environments for broad-spectrum eradication of pathogenic biofilms with biocompatible, non-antibiotic, antimicrobial compositions. In this Example, the inventors observed a rapid and complete biofilm eradication in an in vitro model with synergistic combinations of caprylic and polygalacturonic acids against resistant gram-positive, gram-negative, and fungal biofilms.

In this example, the inventors studied biofilm eradication by the use of medical polygalacturonic acid and caprylic acid (PG+CAP) for potential use in medical applications. In vitro antimicrobial efficacy of PG+CAP was assessed in a well-established biofilm colonization model testing eradication of biofilm following different durations of antimicrobial agent exposure. Biofilm eradication was assessed for clinical isolates of methicillin-resistant *Staphylococcus aureus* (MRSA), multidrug-resistant *Pseudomonas aeruginosa* (PS), and *Candida albicans* (CA) as representative key gram positive, gram negative and fungal infectious pathogens. Briefly, 1 cm silicone discs were placed in 1 mL of human plasma and incubated overnight at 37° C. The plasma was replaced with 1 mL of $5.5 \times 10^5$ CFU/mL inoculum of challenge organism, and incubated for 24 hrs at 37° C. Inoculum was then removed and discs were washed to remove any planktonic organisms by shaking for 30 minutes in 0.9% sterile saline. After washing, discs were exposed to 1 mL of test solution at 37° C. for 15, 30, 60 or 120 minutes. The discs were then removed, placed in 5 mL of 0.9% sterile saline, and sonicated for 15 minutes to disrupt any remaining biofilm. The resulting solution was then cultured and plated on Trypticase Soy Agar+5% sheep blood (bacteria) or Sabouraud Dextrose Agar (yeast). The upper limit of quantitation for this assay was 100 colonies, any plate with >100 colonies was considered to be ">100," which, incorporating the dilution factor, is represented as 5000 in the final colony counts.

Antimicrobial solutions were prepared containing 1% PG (Sigma-Aldrich St Louis, MO. <15% esterified)+0.1% or 0.4% CAP (Sigma-Aldrich, St Louis, MO). The pH was adjusted to 4.0-4.5. Muller Hinton Broth, 1% PG, 0.1% CAP and 0.4% CAP were included as control solutions. The pH of all solutions was adjusted to 4.0-4.5 (except the Muller Hinton Broth control). Complete eradication of the biofilm requires a recovery of no viable colonies following treatment. Recovery of fewer viable organisms than from the control indicates partial eradication of the biofilm. Each time point for each organism for each disinfecting solution was tested in triplicate. Results are presented in FIGS. 1A-C. Complete biofilm eradication required that no viable colonies were recovered following exposure to the test solutions for the specified durations.

As seen in FIGS. 1A-C, protonated CAP has reported weak antimicrobial activity (Skrivanova and Marounek, 2007 and Yang et al., 2010) and PG also has reported weak antimicrobial activity (Thakur et al., 1997). In this study, a synergistic reduction in the time to biofilm eradication is seen with the 1% PG+0.1% CAP solution against CA and PS, and for the 1% PG+0.4% CAP solution against MRSA, PS and CA. One hypothesis for the synergy with the 0.1% CAP combination is that the PG binds important metal ions and cationic molecules such as peptides while the CAP disrupts cell membranes. This concentration of CAP (0.1%) is close to the reported aqueous solubility limit. Without wishing to be bound by any theory, it is envisioned that the enhanced synergy seen with 0.4% CAP might in part be due to apparent solubility enhancement of CAP in the PG+CAP combination. At 0.4% concentration, CAP alone (without PG) showed visible signs of phase separation or immiscibility. Without wishing to be bound by any theory, the inventors anticipate that the partial esterification of the polygalacturonic acid might be important or necessary for balancing the two effects of enhancing the apparent solubility of the CAP while simultaneously binding critical cations.

Efficacy of 1% PG+0.1% CAP in eradicating biofilm was statistically significant relative to both 1% PG alone (p=0.0034) and 0.1% CAP alone (p=0.0034) for MRSA within 1 hour of exposure. Efficacy of 1% PG+0.4% CAP in eradicating biofilm was statistically significant for MRSA (1 hour), PS (30 min), and CA (1 hour) relative to 1% PG along (p=0.0021, p=0.0078, and p<0.001, respectively) and 0.4% CAP alone (p=0.0462, p=0.0109, and p=0.0297, respectively).

CAP is a naturally occurring fatty acid; in the deprotonated state (neutral pH), caprylate ion has a well-established metabolic profile as a nutrient in mammals (Hirabara et al., 2006). Deprotonating CAP can be accomplished by raising the pH above 4.8 (CRC. *Handbook of Chemistry and Physics.* 85 ed. New York, New York: CRC Press; 2004-2005), hence in most physiological environments CAP will rapidly become deprotonated to a benign nutrient once the local pH increases. In a pharmaceutical formulation the antimicrobial protonated CAP state can be maintained with pH below 4.8. This pH falls within range for natural skin pH seen in humans (Lambers et al., 2006). Additional epithelial environments such as the vaginal canal (Lang 1955) and digestive tract (Evans et al., 1988) maintain an acidic pH. Caprylic acid has been reported to aid in wound healing (Srivastava and Durgaprasad, 2008 and Pieper and Caliri, 2003). PG has been widely used in hydrocolloid wound dressings with reported benefits of maintaining a moist, acidic environment and providing a bacterial barrier and is in several commercial wound healing sheet and paste products (Munarin et al., 2012).

Next, PG+CAP combinations were tested using a quantitative assessment of biofilm eradication for PG, CAP and PG+CAP solutions. To assess any potential antimicrobial activity of PG, minimum inhibitory concentration (MIC) assays were conducted. MICs were determined by microbroth dilutions in accordance with CSLI M07 guidelines ((CLSI) CaLSI. M07-A10-Methods for Dilution Antimicrobial Suseptibilty Tested for Bacteria that Grow Aerobically; Approved Standard-Tenth Edition. Volume 35. Wayne, PA2015). MRSA, *Pseudomonas aeruginosa* and *Candida albicans* were exposed to a range of dilutions of PG (0%, 0.25%, 0.5%, 0.75% and 1%). MIC was determined by visual scoring for growth. The well with the lowest concentration of drug in which no turbidity was observed corresponded with the MIC for the organism tested.

For MRSA inhibition occurred at PG concentrations above 0.5%. For *Pseudomonas aeruginosa* inhibition occurred at PG concentrations above 0.75% and for *Candida albicans* growth was not inhibited at PG concentrations of 1% or less.

Figure 2B:
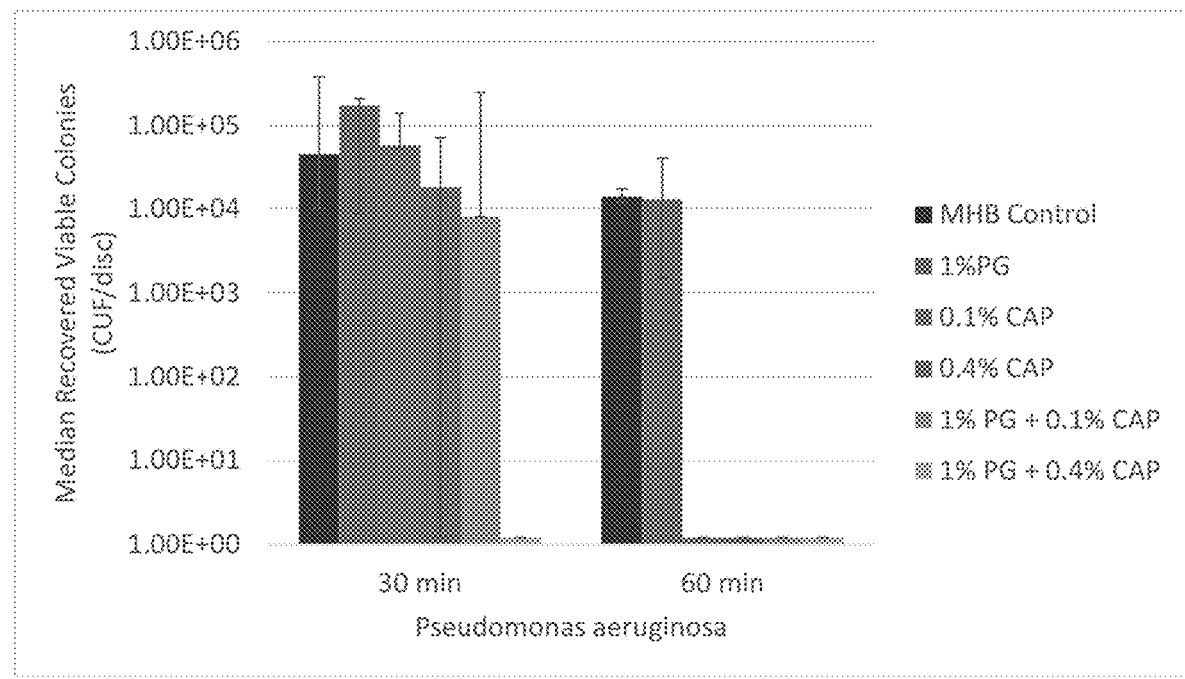
Figure 2C:
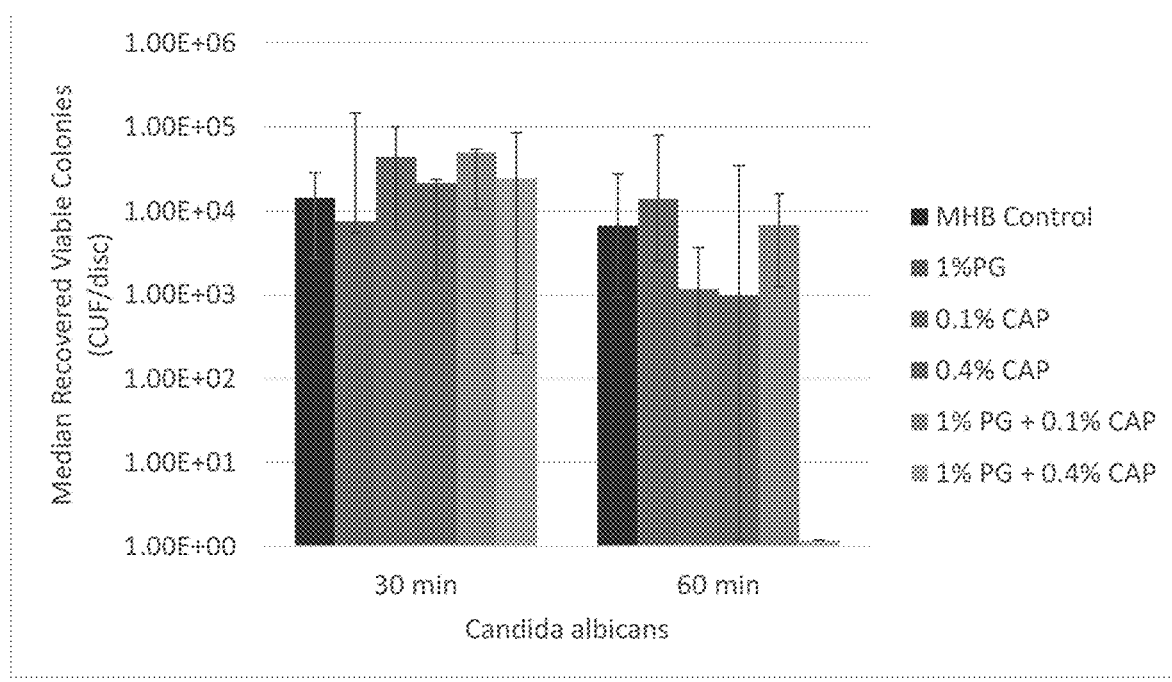

In vitro antimicrobial assessments of PG, CAP, and PG+CAP solutions were conducted using an established time-to-kill biofilm eradication model, the modified Kuhn's model (Kuhn et al., 2002). Briefly, 1 cm diameter silicone discs, were placed into a 24-well tissue culture plate and incubated with donor human plasma at 37° C. for 24 hours. The plasma was then removed, replaced with 1 mL of $5.5 \times 10^5$ CFU of bacterial (MRSA, *Pseudomonas aeruginosa*) or yeast (*Candida albicans*) inocula and incubated at 37 C for an additional 24 hrs. Inoculum was removed and the discs were washed shaking at 100 rpm for 30 minutes in 0.9% sterile saline in order to remove any planktonic organisms. After washing, discs were exposed to 1 mL various disinfectant solutions and incubated at 37° C. for 30 min or 60 min. Saline flush solution was used a negative control. Subsequently, discs were removed and placed in 5 mL of 0.9% sterile saline and sonicated (60 Hz and 150 W) for 15 minutes to disrupt any remaining biofilm. Resulting solutions were quantitatively cultured by plating 100 µL onto Muller-Hinton (for bacteria) or Sabouraud dextrose (for yeast) agar. Antimicrobial solutions were prepared containing 1% PG (Sigma-Aldrich St Louis, MO. <15% esterified)+ either 0.1% or 0.4% CAP (Sigma-Aldrich, St Louis, MO). The pH was adjusted to 4.0-4.5. Muller Hinton Broth, 1% PG, 0.1% CAP and 0.4% CAP were included as control solutions. The pH of all solutions was adjusted to 4.0-4.5 (except the Muller Hinton Broth control). Complete eradication of the biofilm requires a recovery of no viable colonies following treatment. Recovery of fewer viable organisms than from the control indicates partial eradication of the biofilm. All biofilm eradication experiments were performed with 6 replicates, and results are shown in FIGS. 2A-C.

As shown in FIGS. 2A-C, 1% PG+0.4% CAP was able to fully eradicate MRSA biofilms at 60 minutes, *Pseudomonas aeruginosa* biofilm at 30 minutes and *Candida albicans* biofilm at 60 minutes. None of the other solutions were able to fully eradicate biofilms in these time frames.

Statistical analyses: The Kruskal-Wallis test was used to determine whether there was a significant difference in the medians in any of the lock solutions tested. Pairwise comparisons were assessed using the Mann-Whitney U test to cm performance of PG+CAP and CAP lock solutions at specified time points. All tests were 2-sided with an alpha level of 0.5. A P-value less than 0.05 (p<0.05) was utilized to determine statistical significance.

TABLE 1

| Statistical Results |  |
| --- | --- |
| MRSA - 60 min Mann-Whitney - pairwise comparisons - 2-tailed | |
| 1% PG + 0.4% CAP vs Control | p = 0.002 |
| 1% PG + 0.4% CAP vs 1% PG | p = 0.002 |
| 1% PG + 0.4% CAP vs 0.4% CAP | p = 0.180 |
| *Pseudomonas aeruginosa* - 30 min Mann-Whitney - pairwise comparisons - 2-tailed | |
| 1% PG + 0.4% CAP vs Control | p = 0.002 |
| 1% PG + 0.4% CAP vs 1% PG | p = 0.015 |
| 1% PG + 0.4% CAP vs 0.4% CAP | p = 0.041 |
| *Candida albicans* - 60 min Mann-Whitney - pairwise comparisons - 2-tailed | |
| 1% PG + 0.4% CAP vs Control | p = 0.002 |
| 1% PG + 0.4% CAP vs 1% PG | p = 0.002 |
| 1% PG + 0.4% CAP vs 0.4% CAP | p = 0.015 |

At 60 minutes for MRSA, the reductions in viable cells for the 1% PG+0.4% CAP treated samples were significant compared to control and 1% PG. 0.4% CAP was able to reduce, but not completely eradicate viable MRSA organisms in the biofilm with this exposure. At 30 minutes for *Pseudomonas aeruginosa* the reductions in viable cells for the 1% PG+0.4% CAP treated samples were significant compared to control, 1% PG, and 0.4% CAP demonstrating synergy in eradicating *Pseudomonas aeruginosa* biofilm. At 60 minutes for *Candida albicans*, the reductions in viable cells for the 1% PG+0.4% CAP treated samples were significant compared to control, 1% PG, and 0.4% CAP, demonstrating synergy in eradicating *Candida albicans* biofilm.

In conclusion, the inventors observed that PG-CAP combinations are capable of rapidly eradicating gram positive, gram negative and fungal biofilms within 1 hour. This synergistic, non-antibiotic, antimicrobial combination may be used for treating and/or eradicating pathogenic biofilms in medical applications, such as contaminated wounds.

EXAMPLE 2

Non-Antibiotic Wound Ointment for Chronic Wound Therapy

An ointment consisting of a combination of agents including nitroglycerin, caprylic acid, and pectinic acid may be applied topically on the skin of a human patient, and details regarding clinical trials are presented below. Based on the known properties of the individual components, it is anticipated that the use of the combination of nitroglycerin, caprylic acid and pectinic acid will be safe when used in clinically for topical application to the skin. Furthermore, as shown in the above Example, in vitro testing has shown that this mixture are synergistic and highly effective in rapidly eradicating resistant gram positive, gram negative and fungal pathogens embedded in biofilms.

A wound ointment containing nitroglycerin, caprylic acid, and pectinic acid may be used for the topical treatment of chronic wounds that includes venous, arterial, diabetic, and pressure ulcers. This antimicrobial wound ointment with its effect on bacterial killing and increasing blood flow of chronic wounds, targets the important elements and may achieve effective and long-lasting results in the management of patients with chronic wounds. An open-label randomized trial will be performed. Patients presenting with chronic wound including any of the following venous, arterial, diabetic, and pressure ulcers will be randomized to two equal groups: Group 1 will receive the antimicrobial wound ointment, Group 2 will receive the commercially available MEDIHONEY™ ointment as the comparator. The groups will be compared during 12 weeks of treatment for extent of wound-closure, microbial burden, pain and treated-related adverse events. This clinical study will generate preliminary robust data to that may be used to support subsequent future large multicenter clinical trial for the management of chronic wound in cancer patients.

To further assess its clinical utility in healing microbially contaminated wounds, we propose to accomplish the following specific aims in a pilot clinical trial:
(1) To clinically demonstrate reduced microbial burden in wound beds, decrease pain and improved wound closure (such as >50% reduction in wound area) at 6 and 12 weeks with the use of the novel antimicrobial wound ointment versus standard of care wound treatment that include honey.
(2) To clinically demonstrate that the novel antimicrobial wound ointment is well tolerated and safe on wounds as compared to the standard of care ointment.

Microbial contamination of wounds acquired as a result of injury or disease delays healing (Siddiqui and Bernstein, 2010 and Robson 1997). Additional factors complicating healing of infected wounds include vascular disruption which limits delivery of systemically-administered agents to the site of infection, and development of bacterial biofilms in chronically-infected wounds. Biofilms are an essential defense mechanism for microbes, consisting of a 3-dimensional architecture and exopolysaccharide matrix which protects the microbes within from host immune cells, antibodies and antibiotics, and also promotes resistance to antimicrobial therapies. To eliminate biofilm-related infections, it is necessary to penetrate the protective architecture of the biofilm with antimicrobial agents capable of eradicating culprit organisms.

Honey has been used for millennia to aid in healing chronic wounds. Honey exerts several beneficial effects in wounds (6,7) including maintaining an acidic pH (of about 4) through the presence of organic acids, maintaining surface hydration and osmotically debriding wounds through its high sugar content, and inhibiting microbes through release of hydrogen peroxide and presence of other antimicrobial agents (such as methyglyoxal in Manuka honey). Twenty six human clinical trials of honey-based wound treatment have been recently reviewed (8) and showed uneven outcomes. Honey effectively accelerated healing in partial thickness burn wounds and in infected surgical wounds but gave limited evidence of benefit in healing of chronic wounds, pressure and venous ulcers as well as diabetic foot ulcers. MEDIHONEY™ (DermaSciences Inc., Princeton, NJ) is an FDA approved wound ointment that has been subjected to clinical testing relative to standard wound dressing treatments (9,10). MEDIHONEY™ has been reported to reduce pain and necrosis; however, it showed a non-significant trend towards accelerating healing of mixed chronic wounds. Despite some promising studies with honey as an improvement over treatment with standard dressings, there remains a need for an improved antimicrobial wound ointment that can significantly improve outcomes with microbially contaminated chronic wounds.

Data on Antimicrobial Synergy of GTN

Biofilm eradication experiments on caprylic acid—pectinic acid combinations were conducted using the Modified Kuhns Biofilm Eradication Model (Rosenblatt et al., 2015). Methicillin resistant *Staphylococcus aureus* (MRSA), *Pseudomonas aeruginosa* (PS), *Candida albicans* (CA) and *Candida glabarata* (CG) were selected as representative virulent gram positive, gram negative and fungal pathogens causing wound infections for testing. Disinfecting solutions tested in this experiment were 1% pectinic acid, 0.4% Caprylic acid, 0.03% GTN. pH of all disinfecting solutions was adjusted to 4.0-4.5 (same pH range as honey). Reported results are the times (in minutes) to complete biofilm eradication using the biofilm eradication procedure described above. For biofilms that were not completely eradicated within 120 minutes exposure to a disinfecting solution the result is reported as greater than (>) 120 minutes:

TABLE 2

| Disinfecting Solution | MRSA | PS | CA | CG |
|---|---|---|---|---|
| 1% Pectinic Acid (PG) | >120 | 60 | >120 | >120 |
| 0.4% Caprylic Acid (CAP) | 120 | 60 | 120 | 60 |
| 1% PG + 0.4% CAP | 60 | 15 | 30 | 60 |
| 0.03% nitroglycerin (GTN) | >120 | >120 | >120 | >120 |
| 1% PG + 0.4% CAP + 0.03% GTN | 60 | 15 | 30 | 15 |

Data on Catheter Disinfecting Solution Containing CAP/PG and Hydrogen Peroxide

Disinfecting solutions consisting of 0.3% hydrogen peroxide ($H_2O_2$), 1% PG+0.4% CAP+0.3% $H_2O_2$ in 1.5% CMC vehicle were applied around the top external surface and allowed to flow down the external shafts of urinary catheters for a transient contact exposure of a few minutes. The external surfaces had been exposed during the previous 24 hours to either methicillin resistant *Staphylococcus aureus* (MRSA), *Escherichia coli* (*E. coli*), vancomycin resistant *Enterococcus* (VRE) or *Candida albicans* (*C. albi-*

*cans*) as colonizing organisms. 1.5% carboxymethyl cellulose (CMC solution) was used as a control. Median recoveries (in CFU/cm of catheter) from three 1 cm catheter segments are tabulated below:

TABLE 3

| Disinfecting Solution (in 1.5% CMC solution) | MRSA | E. coli | VRE | C. albicans |
|---|---|---|---|---|
| Control | >50,000 | >50,000 | >50,000 | >50,000 |
| 0.3% H2O2 | 0 | 2700 | >50,000 | >50,000 |
| 1% PG + 0.4% CAP + 0.3% H2O2 | 0 | 0 | 0 | 0 |

Only the 1% PG+0.4% CAP+0.3% H2O2 solution was able to completely disinfect the catheter shafts following the transient contact with the disinfecting solutions for all challenge organisms.

Data on Wound Ointment Containing GTN/CAP/PG:

Intrasite™ Gel ointment (Smith and Nephew, Andover, MA) consists of 3% carboxymethylcellulose (CMC) and 20% propyleneglycol (PPG) and has been used for many years in the treatment of chronic wounds (16). The ointment has shown benefit in maintaining hydration and in debriding chronic wounds. A wound healing clinical trial comparing honey to Intrasite™ Gel showed no significant differences in healing benefits (17). An antimicrobial wound ointment was prepared by mixing an aqueous solution of 1% PG, 0.4% CAP, 0.03% GTN, 3% CMC and 20% PPG. This was applied as the disinfecting solution in the biofilm eradication model described above and tested against three recalcitrant bacterial wound contaminants. Controls were the CMC-PPG ointment base and MEDIHONEY™. The bioactive ointment showed rapid biofilm eradication for MRSA, PS, CA and CG (see Table below) with similar eradication times as for the PG+CAP+GTN combination. Time to biofilm eradication (in minutes) for the ointment for additional wound pathogens is also reported in the Table below:

TABLE 4

| | MRSA | PS | CA | CG | Streptococcus pyogenes | Carbapenem-resistant (CRE) Escherichia coli | Vancomycin-resistant Enterococcus (VRE) |
|---|---|---|---|---|---|---|---|
| CMC-PPG ointment base | >120 | >120 | >120 | >120 | >120 | >120 | >120 |
| MEDIHONEY ™ | >120 | 15 | >120 | >120 | >120 | >120 | >120 |
| 1% PG + 0.4% CAP + 0.03% GTN in CMC-PPG ointment | 60 | 15 | 30 | 15 | 15 | 15 | 30 |

Clinical Trial Materials:

Antimicrobial wound ointment. The antimicrobial wound ointment (1% PG+0.4% CAP+0.03% GTN in CMC-PPG ointment base) may be clinically tested for efficacy in healing contaminated wounds. For the proposed trial, the ointment will be packaged for shipping and transport as an aqueous+non-aqueous, two component kit that can be mixed at the point of use. The aqueous component consists of a 0.04% sterile GTN intravenous solution that can be shipped in the sterile containers received from the manufacturer (Baxter, Deerfield, IL). The non-aqueous component consists of: PG and CMC suspended in CAP+PPG liquids. The non-aqueous suspension will be sterilized by gamma irradiation. The two sterile liquids can then be mixed at the point of use by simple exchange between syringes using a sterile luer connector (in approximately a 3:1 volume ratio) such that the final concentrations are 1% PG+0.4% CAP+0.03% GTN in 3% CMC-20% PPG ointment base. This antimicrobial ointment will be prepared and then shipped to the study sites for use.

Commercially available MEDIHONEY™: Honey is essentially a super-saturated solution principally comprising of mixture of sugars together with small quantities of enzymes and amino acids, vitamins, mineral, organic acids, and aromatics responsible for its flavor and odor. MEDIHONEY™ is a standardized widely used medical honey. This honey is sterilized by gamma irradiation to eliminate bacterial spores which are known to be present in regular honey.

Clinical Trial Population:

The clinical study may be an open-label randomized trial between sister institutions. Patients presenting with chronic wound including any of the following venous, arterial, diabetic, and pressure ulcers will be randomized to two equal groups: Group 1 will receive the antimicrobial wound ointment directly applied to wound beds and covered with a suitable dressing. Group 2 will receive the commercially available MEDIHONEY™ ointment as the comparator.

Base line data collection will include gender, age, wound type, size (area and depth) and duration, ulcer location and history of recurrence, stage (I to IV for pressure ulcers), presence of necrosis, granulation and infection, medical history including deep venous thrombosis, hypertension, trauma or surgery to the affected limb, diabetes, immunosuppression and current medications. Patients will be assessed and managed in compliance with locally and nationally accepted guidelines. Reassessment of the wound should be undertaken at every dressing change, and documented at least once weekly or more frequent depending on wound presentation using clinical judgment. Patients will be treated until wound healing or for up to 12 weeks.

Wound Care

The usual proper debridement should be done if needed. Topical ointments consisting of either the antimicrobial wound ointment for group 1 or the MEDIHONEY™ for group 2 will be used twice daily. VAC dressing could be applied on wound with good granulation when applicable. All participants will receive compression bandaging as standard background therapy. Dressing that maintains a moist wound healing environment will be used. A dressing that stays in place, minimizes shear and friction, and does not because additional tissue damage, will be recommended. Wounds must be swabbed if any signs of wound infection is evident by obtaining quantitative tissue biopsies and validated quantitative swab techniques to provide objective evidence of control of the bacterial burden and to help qualify and speciate the offending pathogen. Pain must be assessed on a scale from 0 to 10 and evaluated and recorded weekly. Wound closure should be assessed measured and recorded on healing charts that will record measurements of the wounds at weekly interval. Adverse event should be recorded if it is considered to be related to the study agents. A full wound assessment should be done weekly and the rate of wound healing should be evaluated at the end of the study therapy +/−7 days.

Definitions

Chronic wounds are defined as wounds, which have failed to proceed through an orderly and timely reparative process to produce anatomic and functional integrity over a period of 3 months. Chronic wound are often identified by the presence of a raised, hyperproliferative, yet no advancing wound margin. Pressure ulcers are usually caused by the sustained application of surface pressure over a bony prominence, which inhibits capillary blood flow to the skin and underlying tissue. If the pressure is not relieved it will normally ultimately result in cell death followed by tissue necrosis and breakdown.

Leg or foot ulcers maybe venous, ischaemic, mixed aetiology or traumatic in origin. Infected wound is defined by the presence any of the following: Cellulitis, abscess/pus, increased pain, increased exudate, malodour, delayed healing/deterioration, friable granulation tissue/bleeds easily, Evidence of tracking and temperature.

Patient's Eligibility

Inclusion criteria: Patients must meet the following criteria to be eligible for enrollment into the study: (1) Age>18 years old, (2) Cancer or diabetic patients that had been diagnosed with any of the following chronic wound categories: venous, arterial, diabetic, or pressure ulcers, and (3) Capable of understanding the protocol and providing informed consent.

Exclusion criteria: (1) Patients with allergy to Nitroglycerine, Pectinic acid, Caprilic acid, and MEDIHONEY™, (2) Pregnant women or lactating mother, and/or (3) Wound with osteomyelitis (stage IV pressure ulcers).

Outcomes

The first aim of this trial is the efficacy in wound healing measured by the improvement of wound closure at 6 and 12 weeks in addition to the quantitative microbiological evaluation of bacterial load on infected wounds with the use of the novel antimicrobial wound ointment versus standard of care wound treatment.

The second aim is to evaluate the safety and tolerability of the novel antimicrobial wound ointment as compared to the standard of care ointment by assessing pain and the rates of study wound therapy related adverse events in both groups.

Clinical monitoring. The principle investigator of each collaborating sister institution will be responsible for following the patients and collecting all relevant clinical data including the adverse events that are related to the study therapy.

Statistical Analysis and Sample Size

The aim 1 (efficacy) of the proposed study is to test the null hypothesis that the population proportions of wound healing at 12 weeks, for the Honey treatment group and the antimicrobial wound ointment group, are equal. To test this the inventors may conduct a 2-tailed binary logistic regression analysis with the criterion for significance (alpha) set at 0.050 and that for the power (1-beta) set at 0.80. The rate of missing data could be assumed to be 10%. Our assumption about the effect size is that the proportion with wound healed in the honey treatment group at 12 week is 50% (cite previous study) and relative risk estimate is 1.5. With these assumptions, our required sample size is 98 patients. The sample size calculations are based on "Sample size and optimal design for logistic regression with binary interaction" Demidenko, Statistics in Medicine, 27:36-46.

Our selection for chronic wounds is challenging. Those wounds are consequences of underlying systemic diseases and therefore the successful management of the underlying health problem may contribute to healing to a greater extent than the type of dressing treatment used. In contrast, cases where the underlying health problem may not be easily controlled such as refractory underlying immunosuppression, poorly controlled diabetes, or peripheral vascular diseases non amenable to vascular reconstruction, could result in decrease response to local wound therapy. However, we expect that with our randomization, cases in each category will be equally distributed among both groups. Another possible pitfall is that some patients may miss swab cultures or follow up assessment. These patients will be included in an intent to treat analysis. In addition, every effort will be made to assess all the patients at end of therapy. In order to minimize this bias, a blinded investigator may perform the analysis of the measurement of the wound size, which represents an objective outcome.

It is anticipated that this trial will provide a robust preliminary data, and the trial may be followed by a multicenter, randomized, double-blind control trial comparing this antimicrobial ointment to the standard of care. These therapeutic approaches may be used on high risk cancer and diabetic patients with devastating wound infections and complications. It is anticipated by the inventors that these approaches may substantially improve wound healing in a clinical setting.

EXAMPLE 3

Mammalian Cytotoxicity Testing of PG, CAP and PG+CAP Solutions

Mammalian cytotoxicity testing was conducting following the indirect method of de Gomes et al. (2011) where L929 mouse fibroblasts are exposed to extracts of challenge compositions over a concentration range from 2% to 0.5% for 24 hours. (de Gomes et al., 2011). After exposure viability was tested using the Alamar Blue Assay (O'Brien et al., 2000) and the Trypan Blue Exclusuion assay (Strober W., 2015). L929 Fibroblasts (ATCC #CCL-1; ATCC, Manassas, VA) were maintained in Dulbecco's-modified Eagle's medium (DMEM; Corning Cell Grow, Manassas, VA) supplemented with 10% heat-inactivated fetal bovine serum (FBS; Sigma Aldrich, St. Louis, MO) in 5% $CO_2$ at 37 C. Cells were seeded at a density of $4.5 \times 10^3$ cells/well in 96 well culture plates for Alamar Blue assay and $2.8 \times 10^5$ cells in 25 cm2 culture flasks for live dead staining Following the indirect exposure method of (de Gomes et al., 2011), when growth reached approximately 60% confluence cells were exposed to a 2%, 1%, and 0.5% extracts of 1% PG+0.4% CAP in DMEM+10% FBS for 24 hours. Control, untreated cells were incubated in DMEM+10% FBS. After the exposures, cell viability and toxicity were assessed. All experiments were performed in triplicate.

The Alamar Blue assay (Life Technologies, Corp., Carlsbad CA) was used to assess the sensitivity of metabolic activity of fibroblasts following exposure to PG+CAP. This assay measures the overall metabolic activity based on reduction of resazurin to the highly fluorescent resorufin in response to reductive enzyme activity in cells. Cytotoxic compounds cause fibroblasts to lose their ability to metabolically reduce resazurin to resorufin thus do not produce the fluorescent signal. After 24 hr exposure to PG+CAP solutions, medium was replaced with 100 uL of Hank's Balanced Salt Solution (HBSS; Corning Cell Grow, Manassas, VA)+10% Alamar blue reagent and incubated for 4 hours in 5% CO2 at 37 C. Absorbance was determined at 570 nm using a microplate reader spectrophotometer. Cell viability (absorbance) was compared between treated and untreated control cells. Control, untreated cells were incubated in DMEM+10% FBS. All experiments were performed in triplicate. Results are expressed as a percentage of fluorescent signal normalized to untreated controls.

The Trypan Blue exclusion test was used to determine the number of viable cells present in cell suspension. Live cells with intact membranes have the ability to exclude the dye Trypan Blue, whereas dead cells do not. Therefore viable cells had a clear cytoplasm whereas dead cells presented a blue cytoplasm. After 24 hr exposure to PG+CAP, cells were washed with HBSS to remove any anti-trypsin serum proteins and harvested from the culture flask with 0.05% trypsin EDTA (Corning Cell Grow, Manassas, VA). Once detached, DMEM+10% FBS was added and cells were pelleted at 200×g for 7 minutes. Supernatant was decanted and cells were resuspended in 2 mL of HBSS. Aliquots of 10 uL cell suspension were stained with 10 uL 0.4% Trypan Blue (Sigma Aldrich, St. Louis, MO). Live and dead cells were counted with a hemacytometer. Control, untreated cells were incubated in DMEM+10% FBS. All experiments were performed in triplicate. Results were expressed as percent viable cells in suspension.

Statistical analyses was conducted for comparisons of solutions using a Student's T-test, two tailed, unequal variance. Alpha level was set at 0.05 indicating a P-value<0.05 is significant. Results are shown in FIG. 3.

Figure 3:
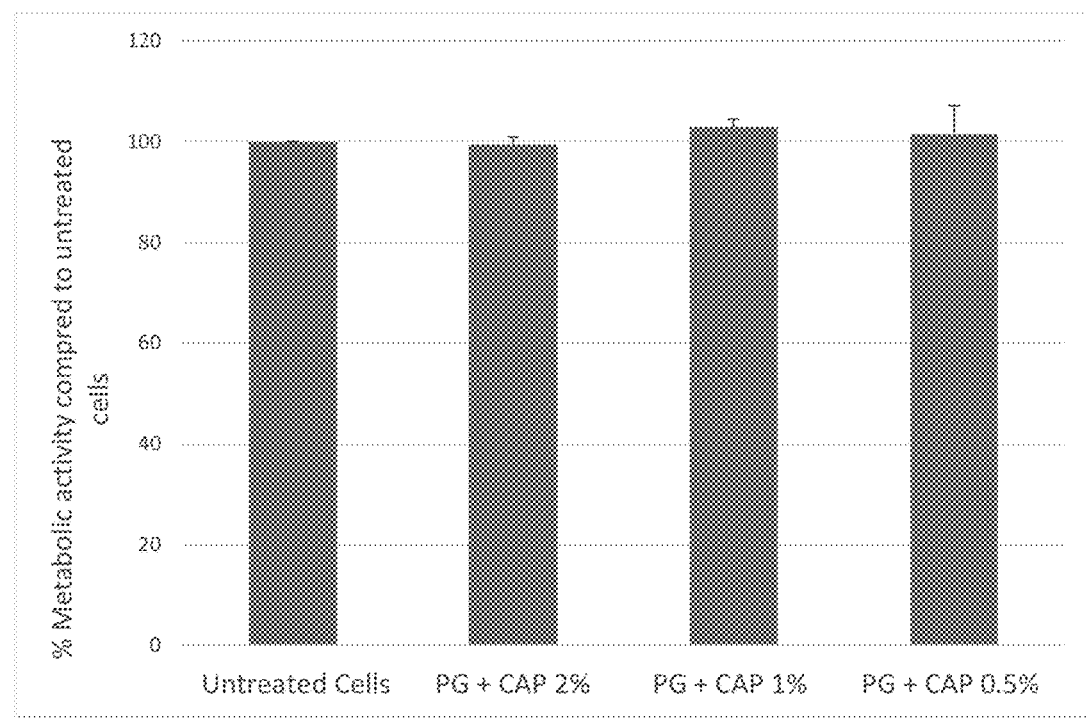
FIG. 3: In vitro cytotoxicity metabolic activity assay results.

In vitro cytotoxicity metabolic activity assay results are shown in FIG. 3. L-929 Fibroblasts were treated with PG+CAP extracts for 24 hours. Cell metabolic activity was assessed with the Alamar Blue assay. Results are expressed as percentage metabolic activity relative to untreated control cells. There were no significant differences (p>0.31) in metabolic activity between any of the groups compared to untreated control cells (by Student's t-test) indicating no appreciable cytotoxicity.

In vitro cytotoxicity cell viability assay results are shown in the table below. L-929 Fibroblasts were treated with PG+CAP extracts for 24 hours. Cell viability was assessed with the Trypan Blue exclusion assay. Results are expressed as percentage viable cells relative to untreated control cells. There was no significant difference (Student's t-test) in cell viability between the groups (p=0.41) indicating no appreciable cytotoxicity.

TABLE 5

Cytotoxicity Cell Viability Assay Results

|  | Untreated L929 Cells (cells/mL) | L929 Fibroblasts treated with 1% PG + 0.4% CAP (cells/mL) |
|---|---|---|
| Mean Live Cells ± standard deviation | $1.84 \pm 0.18 \times 10^6$ | $1.57 \pm 0.11 \times 10^6$ |
| Mean Dead Cells ± standard deviation | $6.00 \pm 2.12 \times 10^4$ | $3.83 \pm 0.60 \times 10^4$ |
| % Viable | 96.89% | 97.62% |

EXAMPLE 4

Assessment of Cytotoxicity of Polygalacturonic Acid+Caprylic Acid+Nitroglycerin Wound Ointment in a Mammalian Fibroblast Model 0.1% Polygalacturonic acid (PG)+0.4% Caprylic Acid (CAP)+0.03% Nitroglycerin (GTN) wound ointment has been shown in Example 3 to be highly effective in eradicating microbial biofilm. The previous experiments demonstrated that PG+CAP is not cytotoxic in a mammalian fibroblast model. In this experiment the cytotoxicity of PG+CAP+GTN in an inert carboxymethylcellulose+propylene glycol ointment base was assessed using a mammalian fibroblast (L929) model of Alamar Blue testing and Trypan Exclusion assay.

Mouse fibroblast cell line, L929, was selected as it has been used previously in mammalian cytotoxicity testing (Sousa de Gomes, et al Cytotoxicity of denture adhesives. Clin Oral Invest. (2011) 15:885-893). Fibroblasts were maintained in Dulbecco's-modified Eagle's medium (DMEM) supplemented with 10% heat-inactivated fetal bovine serum (FBS) in 5% CO2 at 37 C. Cells were seeded at a density of $4.5 \times 10^3$ cells/well in 96 well culture plates for Alamar Blue assay and $2.8 \times 10^5$ cells in 25 cm2 culture flasks for live dead staining. When growth reached approximately 60% confluence cells were exposed to a 2%, 1%, and 0.5% solution of the 1% PG+0.4% CAP+0.03% GTN wound ointment in DMEM+10% FBS for 24 hours (denoted wound 2%, wound 1% and wound 0.5% in the plot below). DMEM+10% FBS was used for control, untreated cells. After exposure drug-induced cell viability and toxicity were assessed with Alamar Blue and Trypan staining for live/dead cell exclusion. All experiments were performed in triplicate.

The Alamar Blue assay (Life Technologies, Corp., Carlsbad CA) was used to assess the sensitivity of fibroblasts to PG+CAP. This assay measured the overall metabolic activity of cells based on reduction of resazurin to the highly fluorescent resorufin in response to reductive enzyme activity in cells (2) Cells sensitive to the experimental drug rapidly lose their ability to metabolically reduce resazurin to resorufin thus do not produce the fluorescent signal. After 24 hr exposure to PG+CAP solutions, medium was replaced with 100 uL of Hank's Balanced Salt Solution (HBSS)+10% Alamar blue reagent and incubated for 4 hours in 5% CO2 at 37 C. Absorbance was determined at 570 nm using a microplate reader spectrophotometer. Cell viability (absorbance) was compared between treated and untreated control cells. Results expressed as a percentage of survival normalized to untreated controls.

Trypan blue exclusion test of cell viability is used to visually determine the number of viable cells present in cell suspension. Live cells with intact membranes have the ability to exclude certain dyes such as trypan blue, whereas dead cells do not. Cells in suspension are stained with 0.4% Trypan blue and counted on a hemacytometer. Viable cells will have a clear cytoplasm, dead cells will have a blue cytoplasm (3). After 24 hr exposure to wound ointment, cells were washed with HBSS to remove any anti-trypsin serum proteins and harvested from the culture flask with 0.05% trypsin EDTA. Once detached, DMEM+10% FBS was added and cells were pelleted at 200×g for 7 minutes. Supernatant was decanted and cells were resuspended in 2 mL of HBSS. Aliquots of 10 uL cell suspension was stained with 10 uL 0.4% trypan blue and live and dead cells were counted with a hemacytometer. Results are expressed as percent viable cells in suspension.

Statistical analyses was conducted for comparisons of solutions using a Student's T-test, two tailed, unequal variance. Alpha level was set at 0.05 indicating a P-value<0.05 is significant.

No toxic effect from solutions of PG+CAP+GTN wound ointment were detected with both the Alamar Blue assay and the Trypan Exclusion Test. The Figure below shows no significant difference between the metabolic activity of cells exposed to solutions of PG+CAP+GTN wound ointment compared to cells grown in DMEM+10% FBS (p>0.09 for all solutions tested). Additionally, no significant difference was detected the percent viability in fibroblasts exposed to PG+CAP+GTN wound ointment compared to untreated control cells (96.43% viable vs 96.8% viable, respectively; p=0.79; Table below)

TABLE 6

Cytotoxicity Results

| | Untreated L929 Cells (cells/mL) | L929 Fibroblasts treated with 2% solution of 1% PG + 0.4% CAP + 300 ug/mL GTN (cells/mL) |
|---|---|---|
| Mean Live Cells ± standard deviation | $1.84 \times 10^6 \pm 1.75 \times 10^5$ | $1.23 \times 10^6 \pm 3.68 \times 10^4$ |
| Mean Dead Cells ± standard deviation | $6.0 \times 10^4 \pm 2.12 \times 10^4$ | $4.60 \times 10^4 \pm 1.98 \times 10^4$ |
| % Viability | 96.89% | 96.43% |

Figure 4:
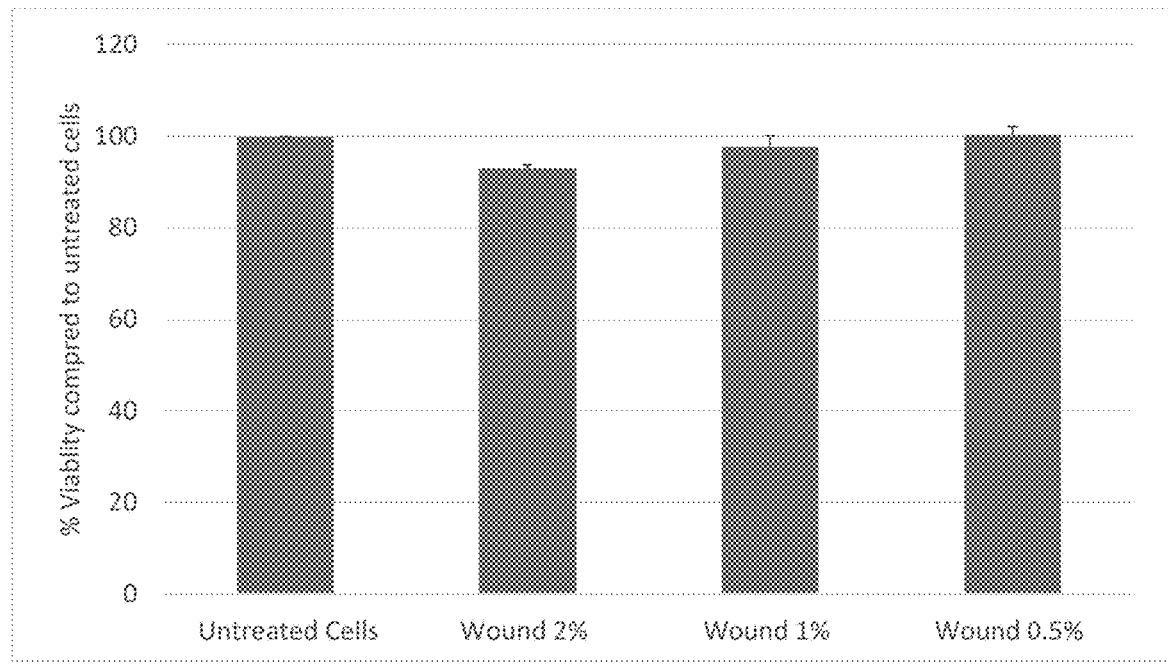
FIG. 4: In vitro cytotoxicity assay results using mammalian fibroblast model.

In vitro cytotoxicity assay results are shown in FIG. 4. L-929 Fibroblasts were treated with PG+CAP+GTN Wound Ointment solutions for 24 hours. Cell viability was assessed with the Alamar Blue assay. Results are expressed as percentage viable cells relative to control untreated cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,217,493
U.S. Pat. No. 5,362,754
U.S. Pat. No. 5,624,704
U.S. Pat. No. 5,688,516
U.S. Pat. No. 5,902,283
U.S. Pat. No. 7,601,731
U.S. Pat. No. 7,651,661
U.S. Patent App. Pub. No. 2005/0197634
U.S. Patent App. Pub. No. 2003/0078242
U.S. Patent App. Pub. No. 2007/0154621
U.S. Patent App. Pub. No. 2008/0183152
U.S. Patent App. Pub. No. 2010/0055086
U.S. Patent App. Pub. No. 2011/0201692
U.S. Patent App. Pub. No. 2012/0064372
Adminstration USFaD. Part 184, Section 1588, Pectins. In: Adminstration USFaD, ed. Code of Federal Regulations Title 21; 2015.
Becker et al., *Int J Toxicol.* 29(3 Suppl): 84S-97S, 2010.
CRC. Handbook of Chemistry and Physics. 85 ed. New York, New York: CRC Press; 2004-2005.
de Gomes et al., Cytotoxicity of denture adhesives. Clin Oral Investig 15:885-893, 2011.
Evans et al., *Gut.* 29(8):1035-41, 1988.
Fenton et al., *Drugs* 66:343-349, 2006.
Haidukewych et al., *Clin Chem.* 28(4 Pt 1):642-5, 1982.
Han et al., *Am J Pathol* 180:1465-1473, 2012.
Hirabara et al., *Biochim Biophys Acta.* 1757(1):57-66, 2006.
James et al., *Wound Repair Regen* 16:37-44, 2008.
Karanlik et al., *Dis Colon Rectum* 52:280-285, 2009.
Kuhn et al., Antifungal susceptibility of *Candida* biofilms: unique efficacy of amphotericin B lipid formulations and echinocandins. Antimicrob Agents Chemother. 2002; 46(6):1773-80
Lambers et al., *Int J Cosmet Sci.* 28(5):359-70, 2006.
Lang, *Obstet Gynecol Surv.* 10(4):546-60, 1955.
Munarin et al., *Int J Biol Macromol.* 51(4):681-9, 2012.
O'Brien et al., Investigation of the Alamar Blue (resazurin) fluorescent dye for the assessment of mammalian cell cytotoxicity. Eur J Biochem 267:5421-5426, 2000.
Pieper and Caliri, 2003.
Rayyan et al., *JPEN J Parenter Enteral Nutr.* 36(1 Suppl): 81S-94S, 2012.
*Remington: The Science and Practice of Pharmacy*, 21$^{st}$ Ed., Lippincott Williams and Wilkins, 2005.
Robson, *Surg Clin North Am* 77:637-650, 1997.
Rosenblatt et al., *Antimicrob Agents Chemother* 59:1786-1788, 2015.
Rosenblatt et al., *Antimicrob Agents Chemother.* 57(8):3555-60, 2013.
Schierle et al., *Wound Repair Regen* 17:354-359, 2009.
Siddiqui and Bernstein, *Clin Dermatol* 28:519-526, 2010.
Skrivanova and Marounek, *Folia Microbiol (Praha).* 52(1): 70-2, 2007.
Sriamornsak, Silpakorn University Journal. 3(1-2):22, 2013.
Srivastava et al., *Indian J Pharmacol.* 40(4):144-6, 2008.
Stoddart et al., *Biochem J.;* 114(4):863-70, October 1969.
Strober W., Trypan Blue Exclusion Test of Cell Viability. Curr Protoc Immunol 111:A3 B 1-3, 2015.
Thakur et al., *Crit Rev Food Sci Nutr.* 37(1):47-73, 1997.
US Department of Health and Human Services CfDCaP. 2013. Antibitoic Resistance Threats in the United States, 2013.
Wanten and Calder, *Am J Clin Nutr.* 85(5):1171-84, 2007.
Yang et al., *Can J Microbiol.* 56(3):263-7, 2010.

What is claimed is:

1. A catheter comprising:
a first end and a second end;
a central lumen extending from the first end and the second end;
a catheter wall disposed around the central lumen, wherein the catheter wall comprises an outer surface;
a first reservoir and a second reservoir;
a first conduit in fluid communication with the first reservoir;
a second conduit in fluid communication with the second reservoir; and
a plurality of outlet ports in in the first reservoir.

2. The catheter of claim 1 further comprising:
(i) a first inlet port in fluid communication with the first conduit; and
(ii) a second inlet port in fluid communication with the second conduit;
wherein the first conduit and the second conduit are located within the catheter wall.

3. The catheter of claim 1 wherein the plurality of outlet ports are arranged circumferentially around the outer surface of the catheter wall.

4. The catheter of claim 1 further comprising a first valve configured to control flow in the first conduit; and further comprising a second valve configured to control flow in the second conduit.

5. The catheter of claim 1 further comprising an irrigation fluid container in fluid communication with the first conduit.

6. The catheter of claim 5 wherein the irrigation fluid container is a first syringe.

7. The catheter of claim 5 wherein the irrigation fluid container is coupled to a pump.

8. The catheter of claim 5 wherein the irrigation fluid container comprises an antimicrobial composition.

9. The catheter of claim 5 wherein the irrigation fluid container is configured to direct irrigation fluid through the first conduit and the plurality of outlet ports in the first reservoir.

10. The catheter of claim 1 further comprising a first inlet port in fluid communication with the first conduit, wherein the first inlet port is proximal to the first end.

11. The catheter of claim 10 further comprising an irrigation fluid container configured to direct irrigation fluid through the first inlet port, the first conduit and the plurality of outlet ports in the first reservoir.

12. The catheter of claim 1 further comprising a pressure source in fluid communication with the second conduit; wherein the pressure source is a second syringe, and wherein the pressure source is configured to inflate the second reservoir via the second conduit.

13. The catheter of claim 12 further comprising a second inlet port in fluid communication with the second conduit, wherein the second inlet port is proximal to the second end; and wherein the pressure source is configured to inflate the second reservoir via the second inlet port and the second conduit.

14. The catheter of claim 1, wherein the catheter is further defined as a long-term catheter.

15. The catheter of claim 1, wherein the long-term catheter is a long term tunneled central venous catheter or a long-term urinary catheter.

16. The catheter of claim 1, wherein the catheter is used to deliver a medicated fluid or a lubricious fluid to an outer surface of the catheter.

17. The method of claim 16, wherein the medicated fluid comprises a pain reliever, antifibrotic agent, mucolytic medication, collagenolytic agent.

18. The method of claim 16, wherein the medicated fluid or the lubricious fluid comprises a fragrance.

19. The catheter of claim 1, comprising any antimicrobial composition.

20. The catheter of claim 1, wherein the catheter comprises three reservoirs.

21. The catheter of claim 1, wherein the catheter comprises three cuffs.

22. The catheter of claim 1, wherein the second reservoir is proximal to the second end; and the first reservoir is located nearer to the first end than the second reservoir.

23. The catheter of claim 22, wherein the catheter is configured to allow an irrigation fluid to flow through the outlet ports and down the outer surface along a pressure gradient directed from the outlet ports towards the first end.

* * * * *